United States Patent
Chapman et al.

(10) Patent No.: US 12,064,307 B2
(45) Date of Patent: *Aug. 20, 2024

(54) MOUTHPIECE FOR TEETH WHITENING

(71) Applicant: SDC U.S. SmilePay SPV, Nashville, TN (US)

(72) Inventors: Josh Chapman, Nashville, TN (US); Melissa French, Nashville, TN (US); Austin Pickett, Nashville, TN (US); Jennifer Kirkpatrick, Nashville, TN (US); Russ Stewart, Nashville, TN (US)

(73) Assignee: SDC U.S. SmilePay SPV, New York, NY (US)

( * ) Notice: Subject to any disclaimer, the term of this patent is extended or adjusted under 35 U.S.C. 154(b) by 145 days.

This patent is subject to a terminal disclaimer.

(21) Appl. No.: 17/498,383

(22) Filed: Oct. 11, 2021

(65) Prior Publication Data
US 2022/0023658 A1   Jan. 27, 2022

Related U.S. Application Data

(63) Continuation of application No. 16/933,569, filed on Jul. 20, 2020, now Pat. No. 11,141,254, which is a
(Continued)

(51) Int. Cl.
*A61C 19/06* (2006.01)
*A61N 5/06* (2006.01)

(52) U.S. Cl.
CPC .......... *A61C 19/066* (2013.01); *A61N 5/0624* (2013.01); *A61N 2005/0606* (2013.01); *A61N 2005/0633* (2013.01)

(58) Field of Classification Search
CPC ............... A61C 19/066; A61N 5/0624; A61N 2005/0606; A61N 2005/0633
See application file for complete search history.

(56) References Cited

U.S. PATENT DOCUMENTS

| 5,316,473 A | 5/1994 | Hare |
| 6,077,073 A | 6/2000 | Jacob |

(Continued)

OTHER PUBLICATIONS

International Search Report and Written Opinion for International Application No. PCT/US2019/044602, mail date Oct. 7, 2019, 13 pages.
(Continued)

*Primary Examiner* — Nicholas D Lucchesi
(74) *Attorney, Agent, or Firm* — Foley & Lardner LLP

(57) ABSTRACT

A whitening light includes a mouthpiece having a light array arranged along the mouthpiece for directing light onto an exposed portion of teeth of a user. The whitening light includes a rear portion comprising a first power source communicably coupled to the light array and a first charging mechanism configured to receive power transferred from a second charging mechanism located on a case for the whitening light. The first power source includes a rechargeable battery charged by the second charging mechanism to a power output sufficient to power the whitening light to emit light configured to whiten teeth upon selection of a button on the rear portion of the whitening light to commence a treatment session, to emit the light for a predetermined duration corresponding to a duration of the treatment session, and to automatically switch the light array to an off-setting following expiration of the predetermined duration.

20 Claims, 14 Drawing Sheets

Related U.S. Application Data continuation-in-part of application No. 16/100,449, filed on Aug. 10, 2018, now Pat. No. 10,716,652.

(56) References Cited

U.S. PATENT DOCUMENTS

| | | | |
|---|---|---|---|
| 6,083,218 A | 7/2000 | Chou | |
| 6,343,933 B1 | 2/2002 | Montgomery et al. | |
| 6,471,716 B1 | 10/2002 | Pecukonis | |
| 6,499,995 B1 | 12/2002 | Schwartz | |
| 6,514,075 B1 | 2/2003 | Jacob | |
| 6,616,447 B1 | 9/2003 | Rizoiu et al. | |
| 6,733,290 B2 | 5/2004 | West et al. | |
| 6,783,363 B2 | 8/2004 | Eguchi et al. | |
| 6,886,567 B1 | 5/2005 | Liu | |
| 6,976,841 B1 | 12/2005 | Osterwalder | |
| 7,114,953 B1 | 10/2006 | Wagner | |
| 7,144,249 B2 | 12/2006 | Rizoiu et al. | |
| 7,331,784 B2 | 2/2008 | Suzuki | |
| 7,384,419 B2 | 6/2008 | Jones et al. | |
| 7,572,124 B2 | 8/2009 | Cipolla et al. | |
| 7,972,024 B2 | 7/2011 | Deleeuw | |
| 7,997,898 B2 | 8/2011 | Ortiz et al. | |
| 7,998,136 B2 | 8/2011 | Jones et al. | |
| 8,029,278 B1 | 10/2011 | Levine | |
| 8,215,954 B2 | 7/2012 | Levine | |
| 8,371,853 B2 | 2/2013 | Levine | |
| 8,591,227 B2 | 11/2013 | Levine | |
| 8,940,033 B2 | 1/2015 | Dwyer et al. | |
| D765,255 S | 8/2016 | Levine | |
| 9,492,257 B2 | 11/2016 | Jablow et al. | |
| 9,572,645 B2 | 2/2017 | Levine et al. | |
| 9,622,841 B2 | 4/2017 | Ajiki et al. | |
| 9,636,198 B2 | 5/2017 | Kodama | |
| 9,730,780 B2 | 8/2017 | Brawn et al. | |
| 9,731,103 B1 | 8/2017 | Rouse | |
| 9,839,500 B2 | 12/2017 | Flyash et al. | |
| 9,889,315 B2 | 2/2018 | Demarest et al. | |
| 9,901,744 B2 | 2/2018 | Demarest et al. | |
| 9,913,992 B2 | 3/2018 | Demarest et al. | |
| 9,974,630 B2 | 5/2018 | Heacock et al. | |
| 10,716,652 B2 | 7/2020 | Stewart et al. | |
| 2005/0202363 A1 | 9/2005 | Osterwalder | |
| 2005/0266370 A1 | 12/2005 | Suzuki | |
| 2006/0019214 A1 | 1/2006 | Lawrence et al. | |
| 2006/0110700 A1 | 5/2006 | Cipolla et al. | |
| 2006/0134576 A1 | 6/2006 | West | |
| 2006/0200212 A1 | 9/2006 | Brawn | |
| 2007/0003905 A1 | 1/2007 | Nguyen et al. | |
| 2007/0037114 A1 | 2/2007 | Wang | |
| 2007/0054233 A1 | 3/2007 | Rizoiu et al. | |
| 2007/0054235 A1 | 3/2007 | Rizoui et al. | |
| 2007/0054236 A1 | 3/2007 | Rizoiu et al. | |
| 2007/0059660 A1 | 3/2007 | Rizoiu et al. | |
| 2007/0248930 A1 | 10/2007 | Brawn | |
| 2008/0044796 A1 | 2/2008 | Hsu | |
| 2008/0063999 A1 | 3/2008 | Osborn | |
| 2008/0113313 A1 | 5/2008 | Khouri | |
| 2008/0233541 A1 | 9/2008 | De Vreese et al. | |
| 2010/0151407 A1 | 6/2010 | Rizoiu et al. | |
| 2010/0305668 A1 | 12/2010 | Brawn | |
| 2011/0076636 A1 | 3/2011 | Wolff et al. | |
| 2011/0091835 A1 | 4/2011 | Levine | |
| 2011/0189626 A1 | 8/2011 | Sanzari | |
| 2012/0045729 A1 | 2/2012 | Ortiz et al. | |
| 2013/0045457 A1 | 2/2013 | Chetiar et al. | |
| 2013/0273490 A1 | 10/2013 | Way et al. | |
| 2013/0280671 A1 | 10/2013 | Brawn et al. | |
| 2014/0121731 A1 | 5/2014 | Brawn | |
| 2014/0242535 A1 | 8/2014 | Lowe et al. | |
| 2015/0064645 A1 | 3/2015 | Jablow et al. | |
| 2015/0132709 A1 | 5/2015 | Park et al. | |
| 2016/0271415 A1 | 9/2016 | Min | |
| 2016/0331487 A1 | 11/2016 | Newman et al. | |
| 2017/0079746 A1 | 3/2017 | Sanders | |
| 2017/0080249 A1 | 3/2017 | Brawn et al. | |
| 2017/0119512 A1 | 5/2017 | Westlake et al. | |
| 2017/0120069 A1 | 5/2017 | Johansson et al. | |
| 2017/0173353 A1 | 6/2017 | Demarest et al. | |
| 2017/0173354 A1 | 6/2017 | Demarest et al. | |
| 2017/0173356 A1 | 6/2017 | Demarest et al. | |
| 2017/0173357 A1 | 6/2017 | Demarest et al. | |
| 2017/0173358 A1 | 6/2017 | Demarest et al. | |
| 2017/0197089 A1 | 7/2017 | Newman et al. | |
| 2017/0197090 A1 | 7/2017 | Newman et al. | |
| 2017/0224455 A1 | 8/2017 | Levine et al. | |
| 2018/0014924 A1 | 1/2018 | Brawn et al. | |
| 2018/0125627 A1 | 5/2018 | Mounce | |
| 2018/0243581 A1 | 8/2018 | Newman et al. | |
| 2019/0000601 A1 | 1/2019 | Huang et al. | |
| 2019/0110746 A1 | 4/2019 | Dau et al. | |
| 2019/0282446 A1 | 9/2019 | Rouse et al. | |
| 2019/0350827 A1 | 11/2019 | Jablow | |
| 2019/0365311 A1 | 12/2019 | Lee | |
| 2020/0121428 A1 | 4/2020 | Pai et al. | |
| 2020/0147473 A1 | 5/2020 | Maloney et al. | |
| 2020/0170574 A1 | 6/2020 | Radmand | |
| 2020/0230432 A1 | 7/2020 | Jablow | |
| 2021/0100645 A1* | 4/2021 | Speicher | A61C 19/066 |
| 2022/0313409 A1* | 10/2022 | Pai | A46B 13/06 |
| 2022/0338968 A1* | 10/2022 | Strotman | A61K 8/22 |
| 2023/0009906 A1* | 1/2023 | Davies-Smith | A61Q 11/00 |
| 2023/0076166 A1* | 3/2023 | Demarest | A61C 19/066 |
| 2023/0139440 A1* | 5/2023 | Nikinmaa | A61N 5/0624 433/215 |
| 2023/0149141 A1* | 5/2023 | Davies-Smith | A61C 19/003 433/29 |
| 2023/0190435 A1* | 6/2023 | Johnson | A46B 15/0028 433/216 |
| 2023/0191143 A1* | 6/2023 | Johnson | A61C 17/221 15/22.2 |

OTHER PUBLICATIONS

International Search Report and Written Opinion for International Application No. PCT/US2021/042143, mail date Aug. 17, 2021, 7 pages.

* cited by examiner

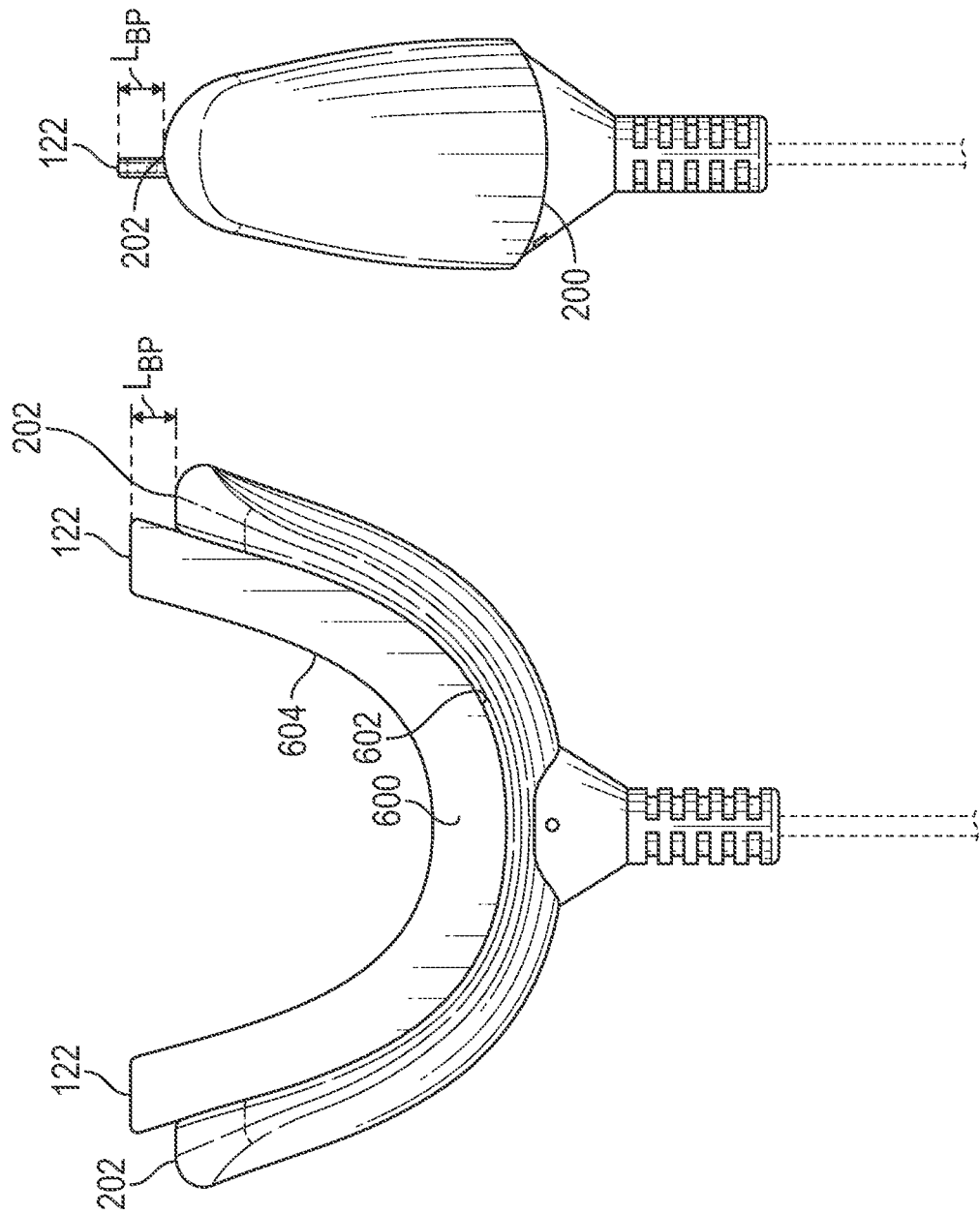

MOUTHPIECE FOR TEETH WHITENING

CROSS-REFERENCE TO RELATED APPLICATIONS

This application is a continuation of U.S. patent application Ser. No. 16/933,569, filed Jul. 20, 2020, which is a continuation-in-part of U.S. patent application Ser. No. 16/100,449, filed Aug. 10, 2018, the contents of each of which are hereby incorporated by reference in their entirety.

BACKGROUND

The present disclosure relates generally to teeth whitening, and more specifically to mouthpieces for teeth whitening.

Various types of teeth whitening treatments exist, including kits and procedures that can be carried out by a user in their own home or in the office of a dental professional. Some teeth whitening kits include trays that a whitening gel is administered to before the trays are positioned in the user's mouth for a duration of time. Some teeth whitening kits include strips that are positioned onto and around the user's teeth for a duration of time. Some teeth whitening procedures include the use of teeth whitening lights located on a teeth whitening apparatus inserted into a user's mouth. However, teeth whitening lights typically direct light on only a limited number of teeth and at undesirable angles and positions, which results in some teeth not being sufficiently whitened leading to inconsistent results. For instance, teeth whitening light mouthpieces do not accommodate for the different dimensional size of the upper teeth with respect to the lower teeth. Additionally, a whitening light mouthpiece may be uncomfortable when positioned in a user mouth due to the dimensions of the mouthpiece and how it fits in the mouth of the user and accommodates their teeth.

SUMMARY

One embodiment relates to a system comprising a whitening light and a case. The whitening light comprises a mouthpiece and a rear portion. The mouthpiece has a first light array arranged along a lower portion of the mouthpiece for directing light onto a plurality of lower teeth of a user and a second light array arranged along an upper portion of the mouthpiece for directing light onto a plurality of upper teeth of the user. The rear portion includes a first charging mechanism and a first power source, where the first power source is communicably coupled to the first light array and the second light array. The case includes a cavity sized to receive the whitening light, a second power source, and a second charging mechanism communicably coupled to the second power source and configured to electrically couple with the first charging mechanism to transfer power from the second power source to the first power source when the whitening light is positioned in the cavity.

Another embodiment relates to a whitening light. The whitening light includes a mouthpiece and a rear portion. The mouthpiece has a first light array arranged along a lower portion of the mouthpiece for directing light onto a plurality of lower teeth of a user and a second light array arranged along an upper portion of the mouthpiece for directing light onto a plurality of upper teeth of the user. The rear portion includes a first power source and a first charging mechanism, where the first power source is communicably coupled to the first light array and the second light array, and where the first charging mechanism is configured to receive power transferred from a second charging mechanism located on a case for the mouthpiece.

Another embodiment relates to a case for a whitening light. The case includes a cavity sized to receive a whitening light configured to whiten teeth, where the whitening light includes a plurality of light arrays, a first power source communicably coupled to the plurality of light arrays, and a first charging mechanism. The case further includes a second power source comprising a rechargeable battery. The case further includes a second charging mechanism communicably coupled to the second power source and configured to electrically couple with the first charging mechanism to transfer power from the second power source to the first power source when the whitening light is positioned in the cavity.

BRIEF DESCRIPTION OF THE DRAWINGS

FIG. 6 is a top view of a mouthpiece for teeth whitening, according to another exemplary embodiment.

FIG. 7 is a side view of the mouthpiece of FIG. 6, according to an exemplary embodiment.

DETAILED DESCRIPTION

Figure 2:
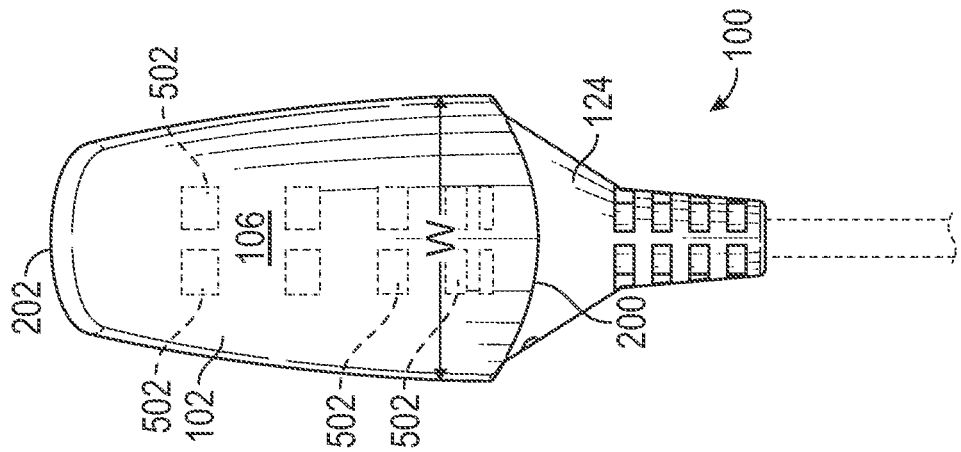
FIG. 2 is a side view of the mouthpiece of FIG. 1, according to an exemplary embodiment.
Figure 1:
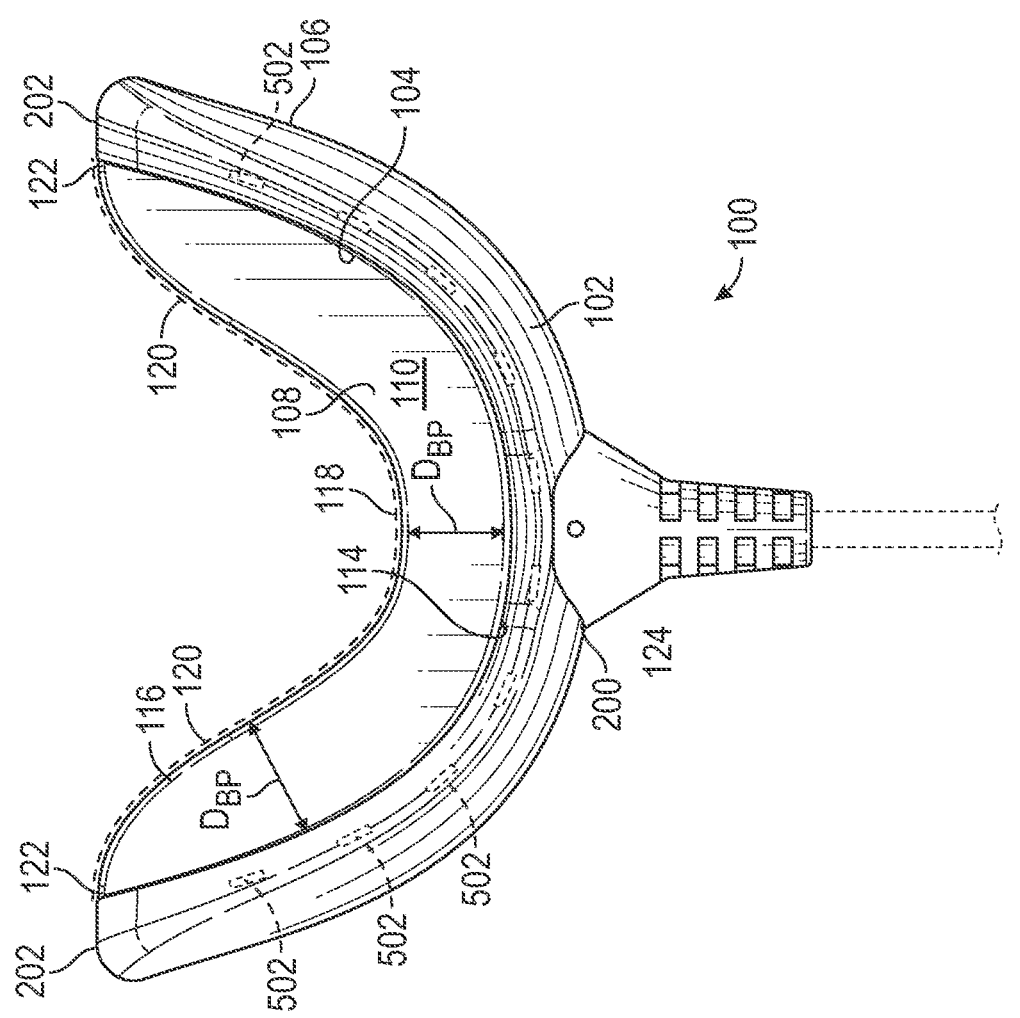
FIG. 1 is a top view of a mouthpiece for teeth whitening, according to an exemplary embodiment.

Referring generally to the figures, a mouthpiece for teeth whitening is disclosed. The mouthpiece is configured for either in-home use, thus eliminating the need to visit a dental professional for a whitening treatment, or for administration to a user by a dental professional. The mouthpiece includes an arch-shaped guard having an inner and outer surface. The inner surface is contoured to follow a shape of a dentition. The arch-shaped guard is sized to span at least a portion of upper teeth and a portion of lower teeth in the dentition. The mouthpiece includes a bite plate positioned along the inner surface and extending substantially perpendicularly therefrom. The bite plate divides the arch-shaped guard into an upper portion for whitening the upper teeth of the user and a lower portion for whitening the lower teeth of the user. The bite plate has an outer profile that follows the contour of the inner surface of the arch-shaped guard. The mouthpiece includes a first light array arranged along the upper portion of the arch-shaped guard, and a second light array arranged along the lower portion of the arch-shaped guard. The first light array and second light array are each arranged in the upper and lower extensions. Accordingly, each of the upper and lower extensions include a respective light array that is arranged to direct light onto a plurality of upper and lower teeth, respectively.

The mouthpiece described herein includes many improvements and advantages over current teeth whitening light systems. For instance, in some embodiments, the light array for the upper and/or lower portions may each include at least ten lights (for a total of twenty lights between both the upper and lower portions) that direct light on at least ten teeth in both the upper and lower jaw of the user. These embodiments expand the number of teeth which are whitened, which may increase user satisfaction.

In some embodiments, lights from the respective light array are arranged different distances from the biteplate based on whether the lights are located on the upper portion of the mouthpiece or the lower portion of the mouthpiece. For example, the distance that the light arrays are arranged from the bite plate can correspond to an average length of the plurality of upper and lower teeth, respectively, such that more light from the light array is distributed to the upper teeth than to the lower teeth, instead of arranging the bite plate in the middle of the light array to equally distribute light from the light array among both the upper teeth and the lower teeth. In these embodiments, light may be directed towards a center of the upper and lower teeth, which may increase the speed and/or consistency of the teeth whitening process and provide better light coverage of the upper teeth, which are typically longer than the lower teeth of a user and therefore have a greater surface area to whiten.

In some embodiments, the bite plate may include an inner profile. A distance between the inner and outer profile may progressively change. For instance, the distance between the inner and outer profile may increase towards an end of the bite plate (e.g., toward an area of the bite plate near a molar of the user). In these embodiments, the bite plate may provide an increased bite surface area. As a result, the user may rely on one or more molar on both the left and right sides of the bite plate and on both the top and bottom of the bite plate to hold the mouthpiece in place, and where whitening gel is administered with the whitening light, gel adherence may also be increased. As such, proper positioning of the mouthpiece within the user's mouth is more likely to be achieved due to the increased bite surface area.

Various other improvements and benefits will become apparent through the subsequent description of the figures.

Referring now to FIG. 1-FIG. 4, various views of a mouthpiece 100 for teeth whitening are shown, according to an exemplary embodiment. The mouthpiece 100 may be sized to fit into a user's mouth. For example, the mouthpiece 100 can be sized for an individual user having a mouth or dentition of a certain size, or mouthpieces 100 of various sizes can be provided such that a particular sized mouthpiece can be selected for a user based on their mouth or dentition size. The mouthpiece 100 can be manufactured such that it is sized to fit all or most users. For instance, the mouthpiece 100 may be manufactured based on consumer data corresponding to impressions of several users (e.g., impressions taken by fifty or more people). In some embodiments, the consumer data is based on dental impressions of consumers receiving a dental treatment or a diagnosis of eligibility for participating in a dental treatment, such as a treatment for aligning one or more teeth of the user (e.g., a dental alignment treatment including the use of dental aligners worn by the user). The mouthpiece 100 may be designed, constructed, manufactured, or otherwise generated based on the impressions of the consumer data. The mouthpiece 100 may have a shape to fit a generic dentition layout which is identified, determined, or otherwise generated based on the impressions of the consumer data. Hence, the mouthpiece 100 may generally have a generic shape sized to fit all users, most users, or an average user. In some embodiments, the mouthpiece 100 may be sized to fit a particular user (e.g., mouthpiece 100 is manufactured based on dental impressions of the particular user). For instance, a user may take an impression of their upper and lower dentitions (e.g., at a dental office, using a home impression kit, etc.), and the mouthpiece 100 may be created, manufactured, or otherwise generated based on the impressions of the user's upper and lower dentitions. Hence, the mouthpiece 100 may be customized for a particular user.

In use, the mouthpiece 100 is positioned in a user's mouth. In some embodiments, whitening gel may be administered on the mouthpiece 100 prior to the mouthpiece 100 being positioned in the user's mouth. The mouthpiece 100 includes lights which direct light on individual teeth to whiten the teeth. The mouthpiece 100 is maintained in the user's mouth for a predetermined treatment time. Following a number of treatments, the user's teeth may become noticeably whiter.

The mouthpiece 100 includes a guard 102 which is shown to be generally arch-shaped, according to an exemplary embodiment. The arch-shaped guard 102 includes an inner surface 104 and an outer surface 106. The inner surface 104 is contoured to follow a shape of a dentition. Accordingly, when the mouthpiece 100 is placed in a user's mouth, the inner surface 104 may generally follow the shape of the user's teeth. Note that the contour for the inner surface 104 may be generic to follow a general shape of a dentition. The guard 102 may be sized to fit comfortably in a user's mouth. The guard 102 may span at least a portion of upper and lower teeth in the dentition. Additionally, the guard 102 may have a thickness $T_G$. In some embodiments, the thickness $T_G$ of the guard 102 may be between 3.25 and 3.50 mm. In some embodiments, the thickness $T_G$ of the guard 102 may be approximately 3.36 mm.

The guard 102 may be formed of a translucent or transparent material. In some embodiments, the guard 102 may be formed of several materials which are joined together. For instance, various layers of the guard 102 may be translucent or transparent, while other layers may be opaque. The guard 102 is shown (in phantom) to include various lights 502 of a light array 500, shown in FIG. 5. The lights 502 may be embedded in the guard 102, or may be arranged along the inner surface 104 of the guard 102. The lights 502 may be arranged to direct light onto the upper and lower teeth of the user, as will be discussed in greater detail below with reference to FIG. 5.

The mouthpiece 100 is shown to include a bite plate 108. In some embodiments, the bite plate 108 and the guard 102 may be integrally formed. In other embodiments, the bite plate 108 may be attached (e.g., adhesively attached, attached with heat) to the guard 102. The bite plate 108 is positioned along the inner surface 104 of the guard 102. The bite plate 108 may be constructed of a foam or rubber-like material. The bite plate 108 may be flexible such that a user can comfortably bite down on the bite plate 108. The bite plate 108 may include an upper surface 110 and a lower surface 112. The upper surface 110 may be the surface which contacts the user's upper (maxillary) teeth in use. The lower surface 112 may be the surface which contacts the user's lower (mandibular) teeth in use. The bite plate 108 may have a thickness $T_B$. In some embodiments, the thickness $T_B$ may be within 1.00 mm and 5.00 mm. For instance, the thickness $T_B$ may be 2.00 mm.

In some embodiments, the bite plate 108 and guard 102 may be formed of a substantially impermeable material. For instance, the bite plate 108 and guard 102 may be formed of a material that is resistant to absorbing or unlikely to be broken down by saliva, water, whitening gel, or other fluids which may contact the bite plate 108 and/or guard 102.

The bite plate 108 is shown to include an outer profile 114 and an inner profile 116. The outer profile 114 may follow the contour of the inner surface 104 of the guard 102. In some embodiments, the outer profile 114 of the bite plate 108 may substantially match the contour of the inner surface 104. Accordingly, where the inner surface 104 is contoured to have an arch, the outer profile 114 may also have an arch. In some embodiments, the inner profile 116 may also be arched. In the embodiment shown in FIG. 1-FIG. 4, the inner profile 116 may be arched in a center portion 118 of the bite plate 108 (e.g., where the incisors would be located in use). Additionally, the inner profile 116 may taper off towards end portions 120 of the bite plate 108 (e.g., where bicuspids and molars would be located in use). According to this embodiment, the inner profile 116 may generally have a bell curve shape.

In some embodiments, a distance $D_{BP}$ between the inner profile 116 and outer profile 114 may change. For instance, the distance $D_{BP}$ between the inner profile 116 and outer profile 114 may progressively increase from the center portion 118 of the bite plate 108 towards the end portions 120 of the bite plate 108. In this regard, the distance $D_{BP}$ may increase towards the ends 122 of the bite plate 108. Additionally, the distance $D_{BP}$ may decrease in the end portions 120 at the ends 122. Accordingly, the distance $D_{BP}$ may progressively increase from the center portion 118 of the bite plate towards the ends 122, and near the ends, the distance $D_{BP}$ may progressively decrease to taper to the ends 122. In these embodiments, a surface area for the bite plate 108 may increase towards the ends 122 of the bite plate 108. As a result, a user may be able to better grip the bite plate 108 with their teeth. The bite plate 108 is shown to extend up to the ends 202 of the guard 102. The bite plate 108 may extend a length which corresponds to a distance between a lateral incisor and a second bicuspid (second pre-molar). In this regard, the bite plate 108 may extend in a user's mouth such that the second bicuspid makes contact with the bite plate 108 in use. In some embodiments, the bite plate 108 may extend a length which corresponds to a distance between a lateral incisor and a first molar (or second molar). Such embodiments may further increase the bite surface area, as will be discussed in greater detail below.

Figure 3:
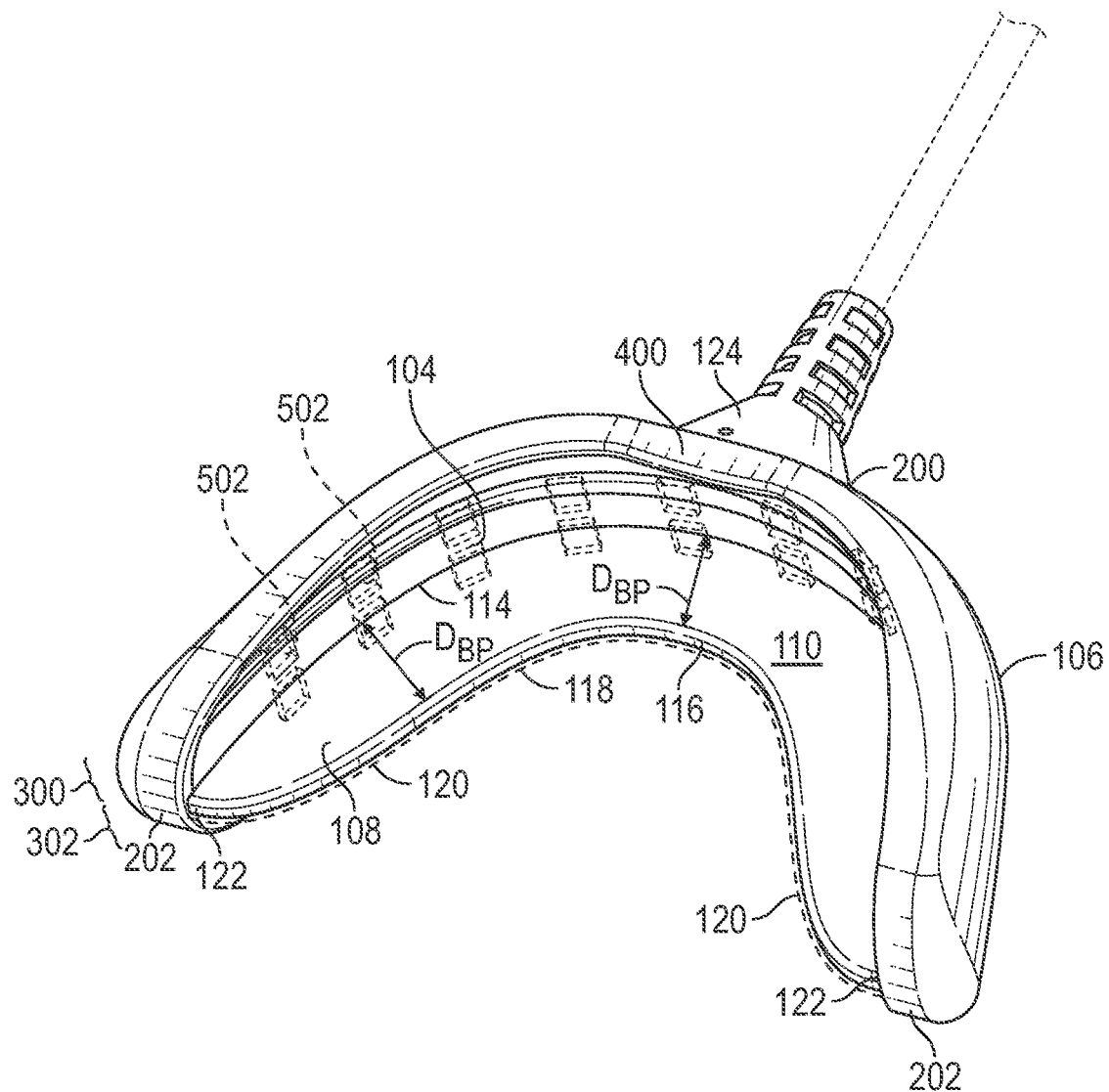
FIG. 3 is a perspective view of the mouthpiece of FIG. 1, according to an exemplary embodiment.
Figure 4:
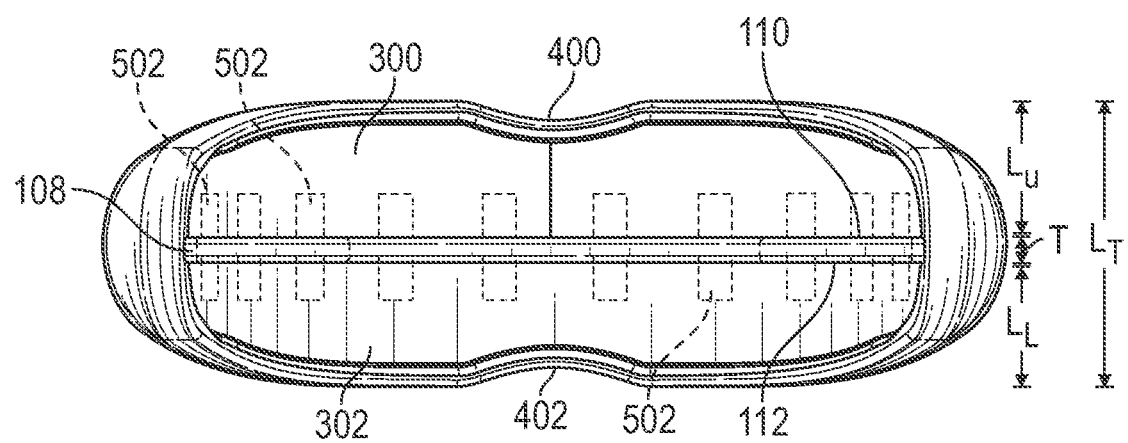
FIG. 4 is a front view of the mouthpiece of FIG. 1, according to an exemplary embodiment.

As can be best seen in FIG. 3 and FIG. 4, the bite plate 108 divides the arch-shaped guard 102 into an upper portion 300 and a lower portion 302. The upper portion 300 may face the upper teeth of the dentition. The lower portion 302 may face the lower teeth of the dentition. The upper portion 300 and lower portion 302 may extend a length $L_U$, $L_L$ from the bite plate 108, respectively. In some embodiments, the length $L_U$ for the upper portion 300 and the length $L_L$ for the lower portion 302 may be substantially the same. In other embodiments, the length $L_U$ for the upper portion 300 may be greater than the length 306 for the lower portion 302. In these embodiments, the length $L_U$ may correspond to an average length of upper teeth of the dentition, and length $L_L$ may correspond to an average length of lower teeth of the dentition. For instance, the upper portion 300 may have a length $L_U$ of between 10.00 mm and 12.00 mm, and the lower portion 302 may have a length $L_L$ of between 9.00 and 11.00 mm. As one non-limiting example, the upper portion 300 may have a length $L_U$ of approximately 11.00 mm and the lower portion 302 may have a length $L_L$ of approximately 10.00 mm. In these embodiments, the upper portion 300 may extend the length of the upper teeth and the lower portion 302 may extend the length of the lower teeth (e.g., at least, the full length of the exposed portion of the central upper and lower incisors).

In some embodiments, the guard 102 may span a length $L_T$ which includes the length $L_U$ of the upper portion 300, thickness T of the bite plate 108, and the length $L_L$ of the lower portion 302. In some embodiments, the guard 102 may span a length $L_T$ of between 20.00 mm and 25.00 mm. In some embodiments, the guard 102 may span a length $L_T$ of approximately 23.00 mm.

As can be best seen in FIG. 2, in some embodiments, a width W of the guard 102 may change from a front end 200 to the back ends 202. For instance, the width W may decrease from the front end 200 to the back ends 202. In this regard, the guard 102 may taper from a front end 200 to the back ends 202 of the guard 102. The guard 102 may taper so as to fit more comfortably in a user's mouth. The width W may be the maximum length $L_L$ (for instance, approximately 23.00 mm) at the front end 200, and the width W may decrease as the guard 102 progresses towards the back end 202.

As can be best seen in FIG. 4, in some embodiments, the guard 102 may have upper and lower detents 400, 402. The upper detent 400 and lower detent 402 may be located towards the front end 200 of the guard 102. The upper detent 400 may accommodate for the maxillary labial frenum of a user. Additionally, the lower detent 402 may accommodate for the mandibular labial frenum of a user. In these embodiments, the upper and lower detent 400, 402 may allow the guard 102 to be comfortably positioned in the user's mouth.

Figure 5:
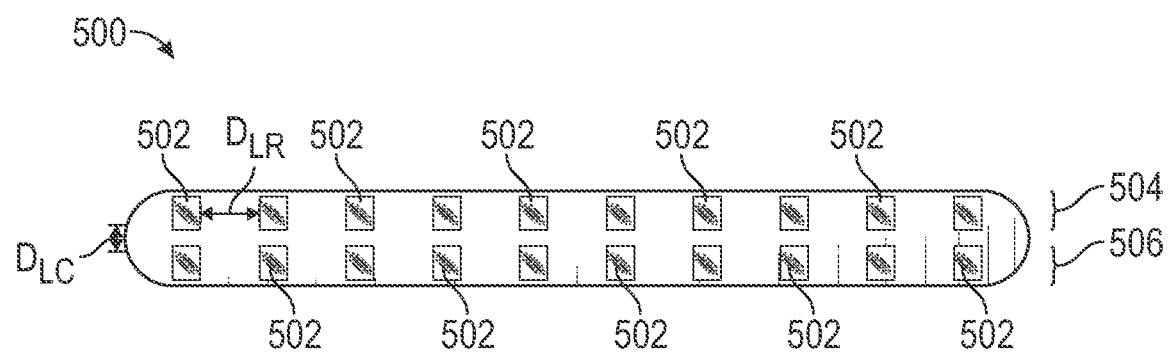
FIG. 5 is a view of a light array for the mouthpiece of FIG. 1, according to an exemplary embodiment.

Referring now to FIG. 1-FIG. 4 and FIG. 5, the guard 102 may include a light array 500. Specifically shown in FIG. 5 is a light array 500 for the mouthpiece 100, according to an exemplary embodiment. The light array 500 is shown to include a plurality of individual lights 502. In some embodiments, the lights 502 may be LEDs. The lights 502 may be structured or configured to output, for instance, ultraviolet light.

The light array 500 is arranged along the inner surface 104 of the guard 102. In some embodiments, the light array 500 may be embedded in the guard 102 with the lights 502 directing light outwardly from the inner surface 104. In other embodiments, the light array 500 may be positioned on the inner surface 104 with the lights 502 facing outwardly from the inner surface 104. In both arrangements, the light array 500 may include a plurality of lights 502 arranged to direct light on a plurality of teeth of the user when in use.

In the embodiment shown in FIG. 5, the light array 500 includes 20 individual lights 502. The light array 500 includes ten upper lights 502, which form an upper light array 504, and ten lower lights 502, which form a lower light array 504. The light array 500 may be positioned along the inner surface 104 such that the lights 502 in the upper light array 504 directs light onto upper teeth, and the lights 502 in the lower light array 506 direct light onto lower teeth. The lights 502 in the upper light array 504 may be arranged along the upper portion 300 of the guard 102, and the lights 502 in the lower light array 506 may be arranged along the lower portion 302 of the guard 102.

The upper light array 504 may be configured to direct light onto each of the maxillary incisors and bicuspids (e.g., pre-molars). The lower light array 506 may be configured to direct light onto each of the mandibular incisors and bicuspids. While 20 individual lights 502 are shown in the embodiment depicted in FIG. 5, the embodiments of the present disclosure are not limited to 20 individual lights and can include more or fewer lights, according to various embodiments and applications.

As shown, the lights 502 are spaced apart from one another. For instance, adjacent lights 502 in the same row (e.g., two lights 502 in the upper light array 504 or lower light array 506) may be separated at a distance $D_{LR}$. The distance $D_{LR}$ may correspond to an average distance between a center of two corresponding adjacent teeth. In some embodiments, the distance $D_{LR}$ may be between 8.00 mm and 10.00 mm. For instance, the distance $D_{LR}$ may be approximately 9.00 mm. Additionally, adjacent lights 502 in the same column (e.g., one light 502 in the upper light array 504 and one light 502 in the lower light array 506) may be separated at a distance DLC. The distance DLC may correspond to an average distance between a center of two corresponding upper and lower teeth. In some embodiments, the distance DLC may correspond to the distance between the center of two corresponding upper and lower teeth and the thickness T of the bite plate 108. In this regard, the adjacent lights 502 in the same column may be positioned to direct light substantially at the center of a corresponding tooth. In these embodiments, the lights 502 directing light substantially at the center of a corresponding tooth may expedite and increase the consistency of the whitening process. In some embodiments, the lights 502 are positioned to direct light substantially at the center of a corresponding tooth where the center is determined based on an intended user, a physical characteristic of the intended user, or a demographic of the intended user.

In some embodiments, the lights 502 may be arranged to direct light substantially at the center of a corresponding tooth based on their position with respect to other lights 502 in the light array 500. According to one embodiment, the bite plate 108 may be positioned along the center of the light array 500. In this embodiment, the lights 502 may be located a distance from the bite plate 108 based on an average length of the upper or lower teeth. The average length of the upper or lower teeth may be an average of all upper teeth (or lower teeth), or the average length of the upper or lower teeth may be an average of a subset of the upper teeth (or lower teeth).

In arrangements where the length $L_U$ of the upper portion 300 and length $L_L$ of the lower portion 302 are different, the lights 502 in the upper and lower light arrays 504, 508 may be located at different distances from the bite plate 108. For instance, each of the lights 502 in the upper light array 504 may be located at a first distance from the bite plate 108 which corresponds to half of the length $L_U$ of the upper portion 300. In these embodiments, the lights 502 in the upper light array 504 may be positioned in the center of the upper portion 300. Similarly, each of the lights 502 in the lower light array 506 may be located at a second distance from the bite plate 108 which corresponds to half of the length $L_L$ of the lower portion 302. In these embodiments, the lights 502 in the lower light array 506 may be positioned in the center of the lower portion 302.

In arrangements where the length $L_U$ of the upper portion 300 and length $L_L$ of the lower portion 302 are substantially the same, the lights 502 in the upper and lower light arrays 504, 508 may be located at different distances from the bite plate 108 and not located in the center of their respective upper portion 300 and lower portion 302. For instance, each of the lights 502 in the upper light array 504 may be located at a first distance from the bite plate 108 which corresponds to half of the average length of upper teeth of the dentition, and each of the lights 502 in the lower light array 504 may be located at a second distance from the bite plate 108 which corresponds to half of the average length of lower teeth of the dentition. In these embodiments, the lights 502 in the upper light array 504 may be positioned in the center of the upper portion 300. Similarly, each of the lights 502 in the lower light array 506 may be located at a second distance from the bite plate 108 which corresponds to half of the length $L_L$ of the lower portion 302. In these embodiments, the lights 502 in the lower light array 506 may be positioned in the center of the lower portion 302.

Each of the lights 502 may receive power from an external source. For instance, the mouthpiece 100 may include an adapter 124 which extends from the front end 200 of the guard 102. The adapter 124 may electrically couple the external source to the mouthpiece 100 and each of the individual lights 502. The external source may provide electrical power to each of the lights 502 such that the lights 502 can direct light onto each of the individual corresponding teeth. In some embodiments, the mouthpiece 100 with the adapter 124 may extend a distance D. The distance D may correspond to the distance which the mouthpiece 100 extends into the user's mouth, and the length of the adapter 124. In some embodiments, the distance D may be between 50.00 mm and 60.00 mm. In some embodiments, the distance D may be 57.00 mm. For instance, the adapter 124 may have a length of approximately 18.00 mm, and the mouthpiece 100 may extend in the user's mouth a distance of approximately 39.00 mm. In these embodiments, the mouthpiece 100 may sit comfortably within the user's mouth.

Referring now to FIG. 6-FIG. 10, in some embodiments, various modifications may be made to the bite plate 102. Specifically, FIG. 6-FIG. 10 each show various views of a mouthpiece for teeth whitening, according to exemplary embodiments. The mouthpieces depicted in FIG. 6-FIG. 10 may include many of the same features as those described above with reference to FIG. 1-FIG. 5. Accordingly, these reference numerals will be duplicated for purpose of clarity.

As shown in FIG. 6, in some embodiments, bite plate 600 may have a different shape than bite plate 108. For instance, bite plate 600 may have an inner and outer profile 602, 604 which are substantially the same. In this embodiment, the inner profile 602 and outer profile 604 may both be arched. The inner and outer profile 602, 604 may be arched to substantially match the contour of the inner surface 104 of the guard 102.

In some embodiments, the bite plate 600 may extend past the back ends 202 of the guard 102. For instance, as can be best seen in FIG. 6 and FIG. 7, the bite plate 600 may extend a length LBP past the back ends 202. The ends 122 of the bite plate 600 may extend the length LBP past the back ends 202 of the guard 102. In some embodiments, length LBP may be between 3.00 mm and 7.00 mm. For instance, the length LBP may be 5.00 mm. In these embodiments, the bite plate 600 may be extended to provide an increased bite surface area for a user. Such embodiments may improve adherence of gel on the user's teeth (since the position of the mouthpiece 100 will likely be maintained with an increased bite surface area). Additionally, such embodiments may improve the likelihood of proper positioning of the mouthpiece 100 within the user's mouth based on the increased surface area.

Figure 8:
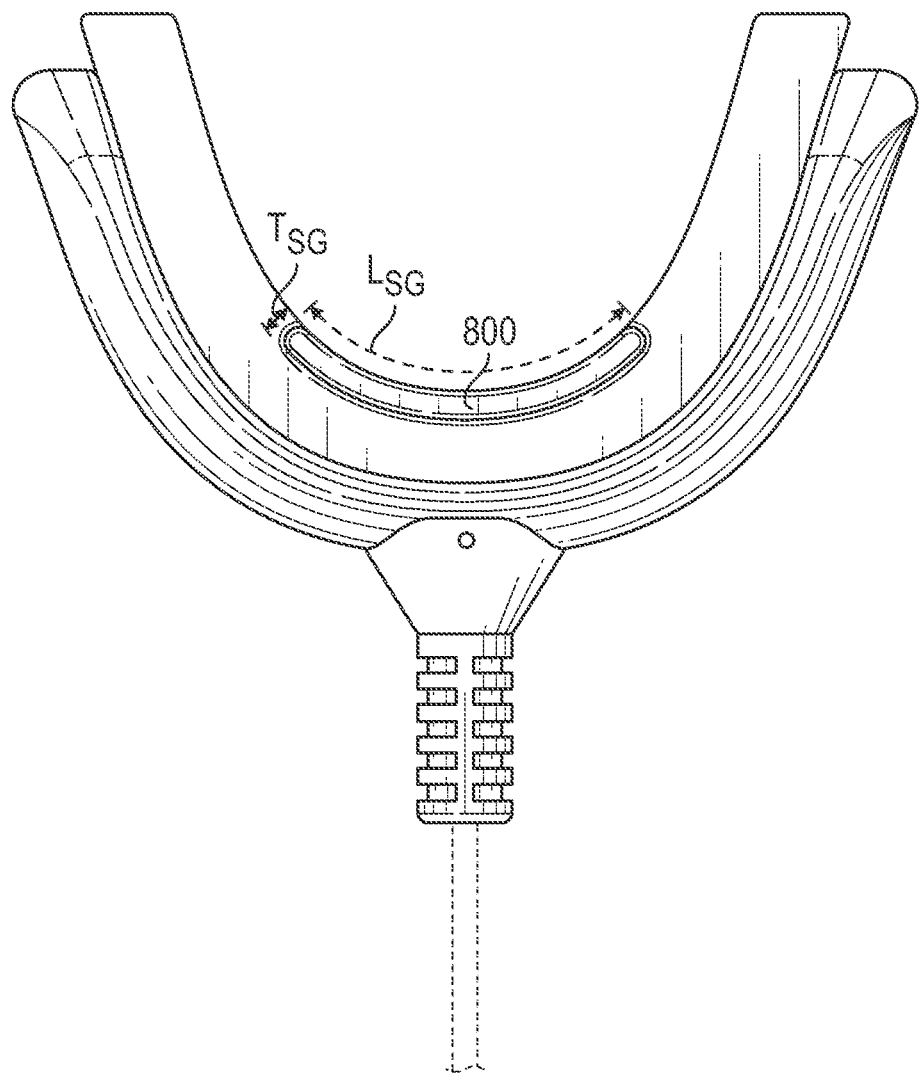
FIG. 8 is a top view of a mouthpiece for teeth whitening, according to another exemplary embodiment.
Figure 9:
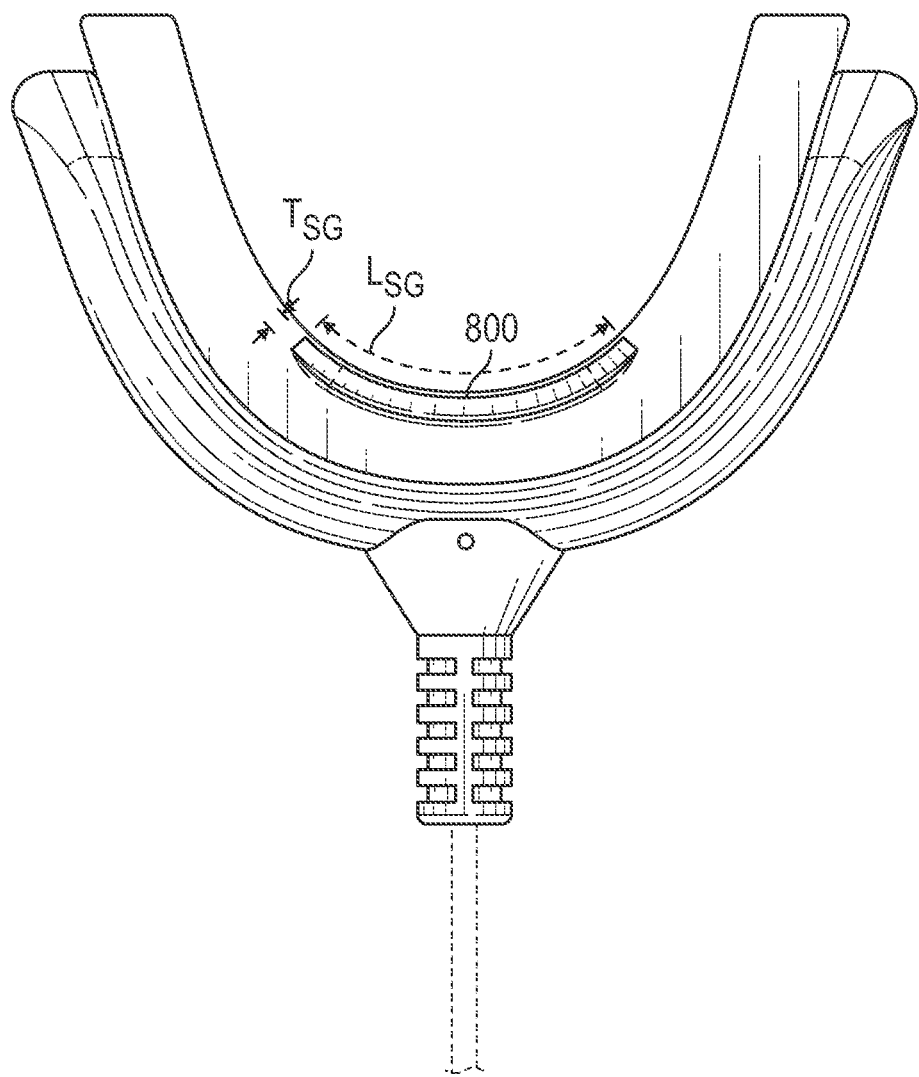
FIG. 9 is a top view of a mouthpiece for teeth whitening, according to another exemplary embodiment.
Figure 10:
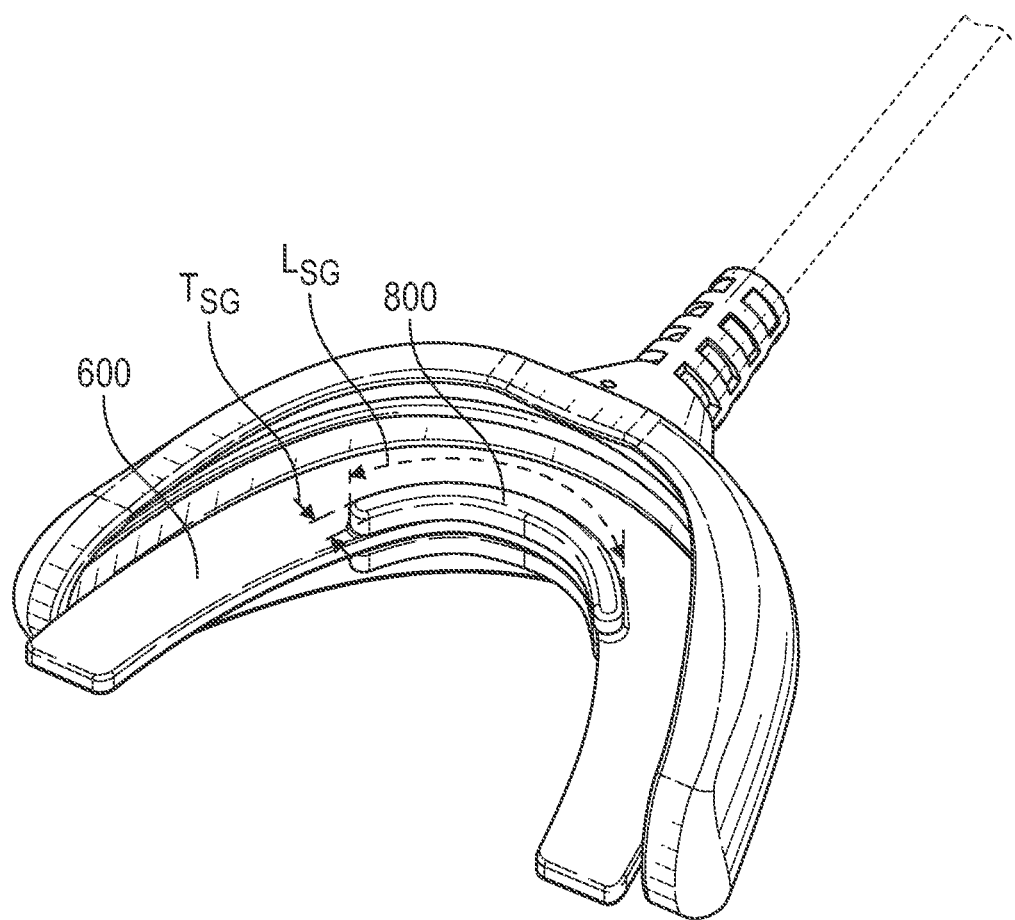
FIG. 10 is a perspective view of a mouthpiece for teeth whitening, according to another exemplary embodiment.

As can be best seen in FIG. 8-FIG. 10, in some embodiments, the bite plate 600 (or bite plate 108) may include a slip guard 800. The slip guard 800 may be located near the center of the bite plate 600. The slip guard 800 may be positioned along a portion of the inner profile 602 of the bite plate 600. The slip guard 800 may be positioned on the upper surface 110 and/or the lower surface 112. In some embodiments, the bite plate 800 may include two slip guards 800 (e.g., upper and lower slip guards 800).

The slip guard 800 may be sized to fit behind a user's teeth when in use. For instance, the slip guard 800 may have a thickness TSG and a length LSG. The thickness TSG may be between 1.00 mm and 4.00 mm. For instance, the thickness TSG may be approximately 2.50 mm. Additionally, the length LSG may extend the length of the central and lateral incisors in a dentition. In some embodiments, the length LSG may extend the length of the central incisors, lateral incisors, and cuspids, for instance. Accordingly, the user positions the mouthpiece 100 in their mouth where their teeth are sandwiched between the slip guard 800 and the inner surface 104 of the guard 102. The slip guard 800 may have flat ends, such as the slip guard 800 depicted in FIG. 8. Additionally, the slip guard 800 may have rounded or beveled ends, such as the slip guard 800 depicted in FIG. 9.

Figure 11:
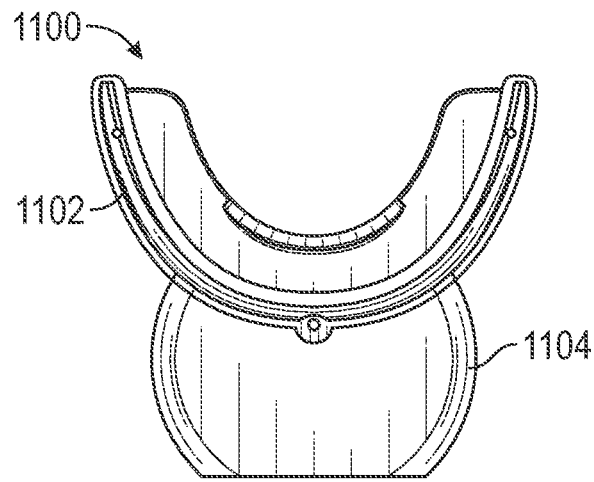
FIG. 11 is a top view of a whitening light, according to another exemplary embodiment.
Figure 12:
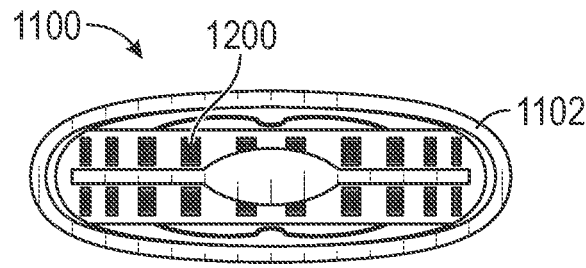
FIG. 12 is a front view of the whitening light of FIG. 11, according to an exemplary embodiment.
Figure 13:
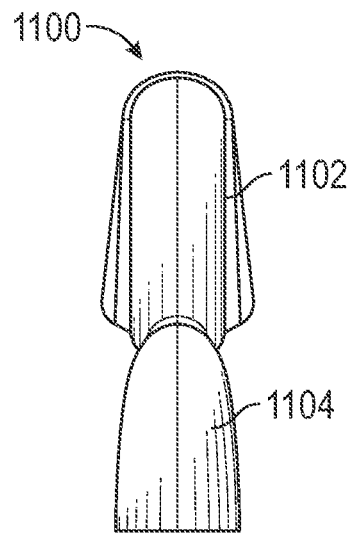
FIG. 13 is a side view of the whitening light of FIG. 11, according to an exemplary embodiment.
Figures 14, 15:
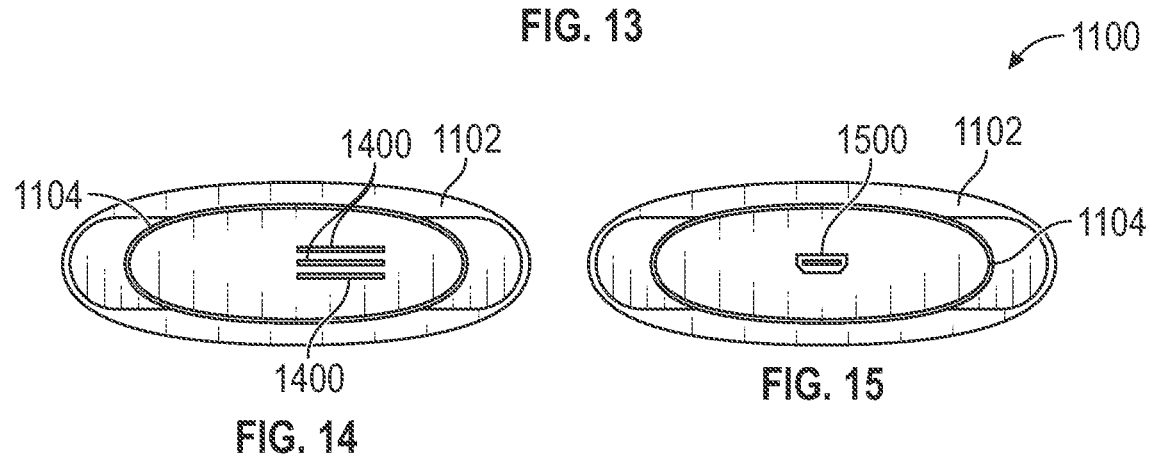
FIG. 14 is a first embodiment of a back view of the whitening light of FIG. 11, according to an exemplary embodiment.
FIG. 15 is a second embodiment of a back view of the whitening light of FIG. 11, according to another exemplary embodiment.

Referring now to FIG. 11-FIG. 15, depicted are various views of another embodiment of a whitening light 1100. Specifically, FIG. 11 shows a top view of the whitening light 1100, FIG. 12 is a front view of the whitening light 1100, FIG. 13 is a side view of the whitening light 1100, FIG. 14 is a back view of the whitening light 1100 according to a first embodiment, and FIG. 15 is a back view of the whitening light 1100 according to a second embodiment.

As best seen in FIG. 11 and FIG. 12, the whitening light 1100 may include a front portion having a mouthpiece 1102 and a rear portion 1104. The mouthpiece 1102 may be similar in some respects to the mouthpiece 100 described above with reference to FIG. 1-FIG. 10. The mouthpiece 1102 may be formed of an antimicrobial silicon which is to be situated in a user's mouth. The mouthpiece 1102 may include a plurality of LEDs 1106 configured to output light which reacts with a solution applied to a user's teeth to whiten the user's teeth. In some embodiments, the mouthpiece 1102 may include 20 LEDs 1106 (e.g., ten LEDs 1106 for whitening the user's upper dental arch and ten LEDs 1106 for whitening the user's lower dental arch), though more or fewer LEDs 1106 may be included. In some embodiments, the LEDs 1106 may be configured to output light in a particular frequency within the electromagnetic spectrum. For example, the LEDs 1106 may be configured to output light in the ultraviolet to blue frequency spectrum. For example, the LEDs 1106 may be configured to output a mix of blue (e.g., 440 nm-490 nm), purple (400 nm-440 nm), and ultraviolet (10 nm-400 nm) light. In some instances, the ultraviolet light may react with the solution applied to the user's teeth, while the mixture of blue and purple light provides an aesthetically pleasing light when in use. In some embodiments, the LEDs 1106 may be configured to output light in or near the green frequency spectrum (500-565 nm). Such embodiments may provide for both therapeutic and whitening effects. In some embodiments, a user may switch between different lighting effects. For example, and as described in greater detail below, a user may provide an input to an application which switches between a first color scheme (e.g., blue/purple) to a second color scheme (e.g., green), or a third color scheme (e.g., red). The application may transmit a command (either directly or indirectly) to the whitening light 1100 to cause the LEDs 1106 to output light according to the selected color scheme.

The whitening light 1100 may include a rear portion 1104. The rear portion 1104 may be structured of a lightweight material, such as a resin, plastic, or other polymeric material which is lightweight. As best shown in FIG. 13, the whitening light 1100 may have a side profile which is similar to the mouthpiece 100 shown in FIG. 2 and FIG. 7. However, the rear portion 1104 may extend outwardly from a backside of the mouthpiece 1102.

The rear portion 1104 may be configured to house a power source. The power source may include a plurality of rechargeable batteries (such as Li-ion batteries). The power source may be self-contained within the rear portion 1104, such that a user can maintain the whitening light 1100 in their mouth without the use of their hands (e.g., to support an external power source, such as an external charger, a battery pack, or their mobile device). The power source may be communicably coupled to the LEDs 1106. Accordingly, the power source may be configured to power the LEDs 1106 to output light onto the user's teeth when in use. The power source may be designed to maintain a charge sufficient to output light for a predetermined amount of time suitable for whitening teeth. Such embodiments may result in limiting the overall profile of the rear portion 1104 through a reduced-sized battery bank. For example, the power source may be designed to maintain a charge sufficient to output light for a predetermined duration, such as three minutes, four minutes, five minutes, six minutes, seven minutes, eight minutes, nine minutes, ten minutes, 15 minutes, 20 minutes, 30 minutes, etc. Such a duration may be suitable for whitening teeth, but may require fewer or smaller individual rechargeable batteries in the power source. For example, the power source may be designed to provide between 40 to 80 mAh such that the whitening light 1100 can output light for the predetermined duration.

In some embodiments, the whitening light 1100 may be configured to automatically output light once removed from a source of a charge. The whitening light 1100 may then output light until the power source is depleted (e.g., following the predetermined duration), and automatically deactivate. Such embodiments may ensure that users do not maintain the whitening light 1100 in their mouths in excess of the predetermined duration. In some embodiments, the whitening light 1100 may include one or more feedback devices (such as a haptic feedback device, a speaker, etc.), which alert the user when the predetermined duration has elapsed. For example, the feedback device may vibrate the whitening light 1100, play a chime or noise, etc. once the predetermined duration has elapsed. Such embodiments may also ensure users do not maintain the whitening light 1100 in their mouths in excess of the predetermined duration.

As shown in FIG. 14 and FIG. 15, the power source may be configured to be charged via an external source. For example, in the embodiment shown in FIG. 14, the power source of the whitening light 1100 may be configured to be charged via a charging mechanism 1400 (e.g., one or more charging plate, charging pin, requiring contact or by no contact charging, etc.). The charging mechanism 1400 may be arranged along a backside of the rear portion 1104 as shown in FIG. 14. In some embodiments, the charging mechanism 1400 may be arranged along a top or a bottom of the rear portion 1104. The charging mechanism 1400 may function in a manner similar to surface-contact charging. For example, the charging mechanism 1400 may interface with a corresponding charging mechanism to form a surface contact and exchange power therethrough (e.g., to charge the power source of the whitening light 1100). Such embodiments may provide a waterproof whitening light 1100 (with a rating of up to IP69K) to permit whitening, for example, in a shower or bathtub.

In the embodiment shown in FIG. 15, the power source of the whitening light 1100 may be configured to be charged via an external charger or power source using an adapter, such as a USB type-C adapter, micro-USB adapter, or other adapter, which is inserted into a port 1500 of the whitening light 1100. A user may insert one end of the adapter into the port 1500 of the whitening light 1100, and insert the other end of the adapter into an external charger or power source (such as a wall outlet, a mobile phone, a computer, a battery pack, etc.). In some embodiments, the whitening light 1100 may include both the port 1500 and the charging mechanism 1400. For example, the port 1500 may be arranged along a backside of the rear portion 1104, and the charging mechanism may be arranged along a top or bottom of the rear portion 1104. The charging mechanism 1400 may function as a primary source for charging the power source of the whitening light 1100, and the port 1500 may function as a back-up source for charging the power source of the whitening light 1100 (in the event of a user losing the case, the case breaking, etc.).

Figure 16:
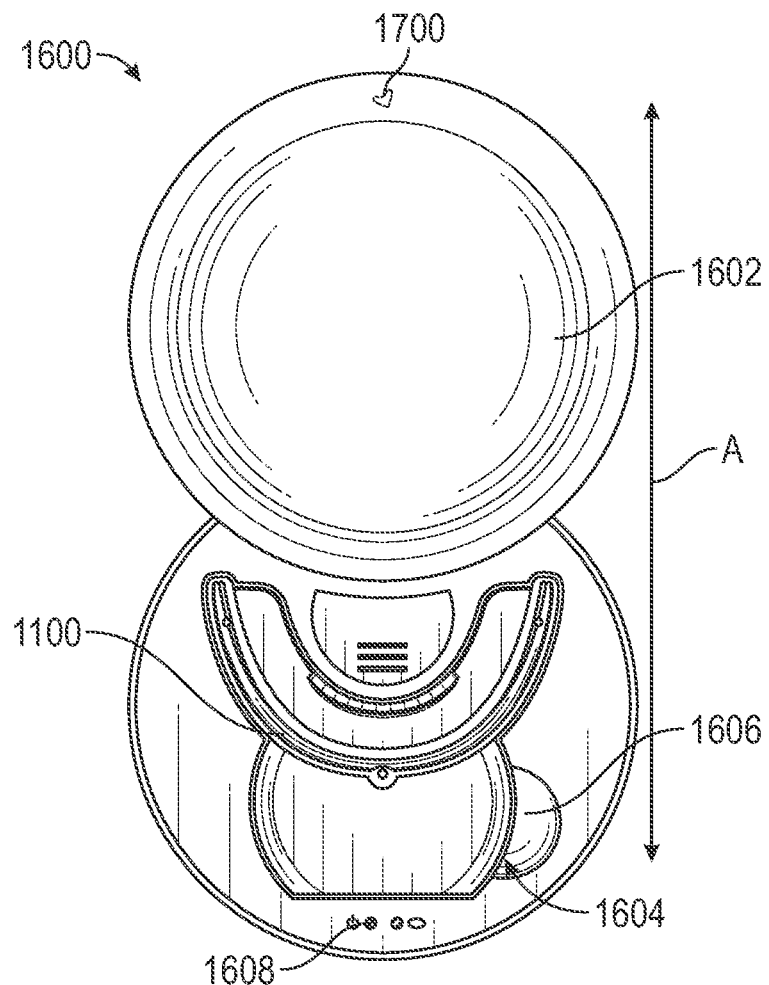
FIG. 16 is a top open view of a case for a whitening light, according an exemplary embodiment.
Figure 17:
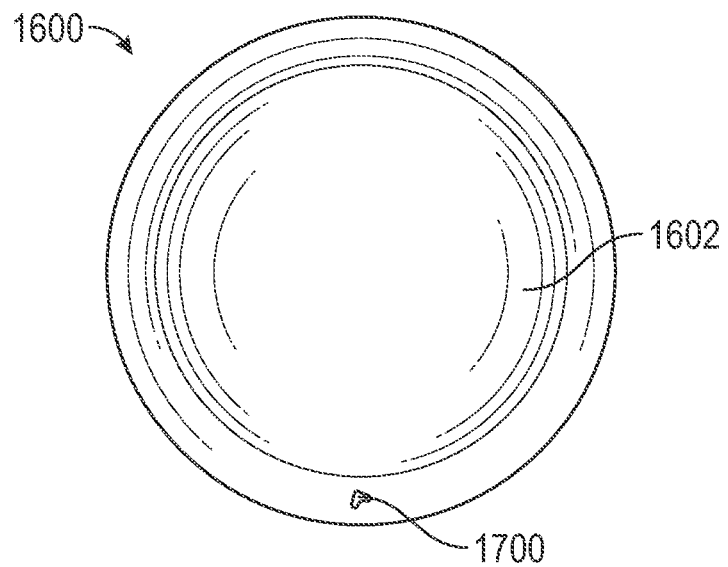
FIG. 17 is a top closed view of the case of FIG. 16, according to an exemplary embodiment.
Figure 18:
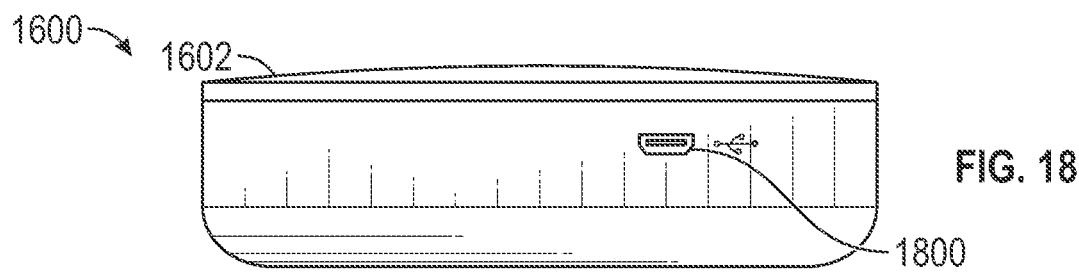
FIG. 18 is a back view of the case of FIG. 16, according to an exemplary embodiment.
Figure 19:
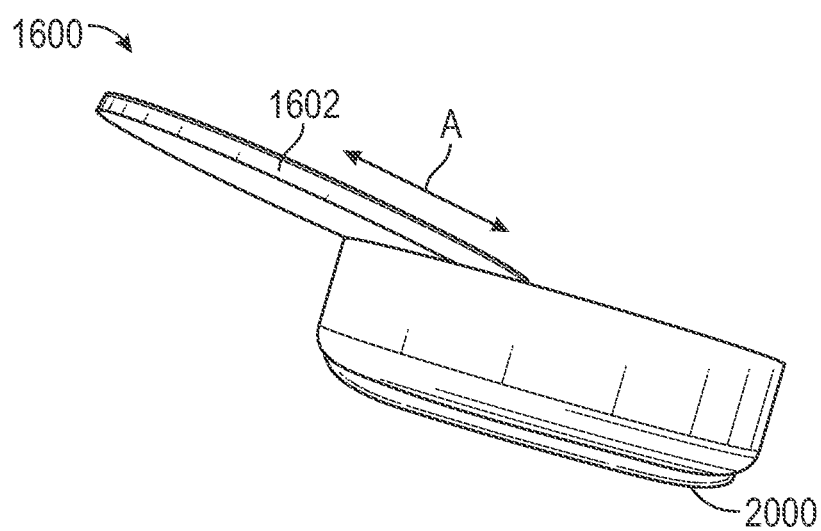
FIG. 19 is a side perspective view of the case of FIG. 16 having a first embodiment of an opening mechanism, according to an exemplary embodiment.
Figure 20:
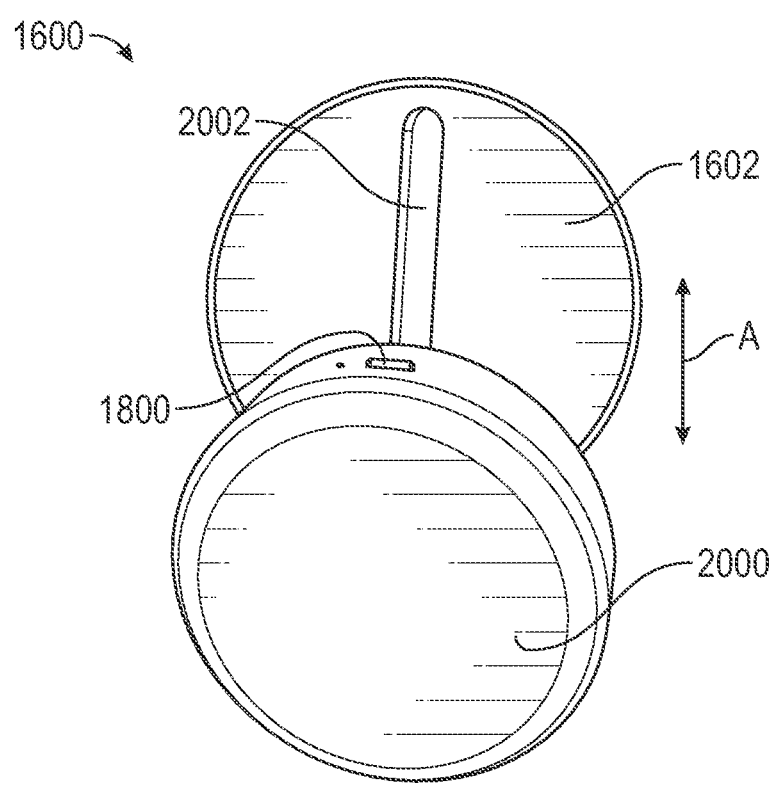
FIG. 20 is a bottom view of the case of FIG. 16 having a second embodiment of an opening mechanism, according to another exemplary embodiment.

Referring now to FIG. 16-FIG. 20, depicted are various views of a case 1600 for a whitening light, such as the whitening light 1100 shown in FIG. 11-FIG. 15, or the mouthpiece 100 for a whitening light shown in FIG. 1-FIG. 10. Specifically, FIG. 16 is a top open view of a case 1600, FIG. 17 is a top closed view of the case 1600, FIG. 18 is a back view of the case 1600, FIG. 19 is a side perspective view of the case 1600 in an open position, and FIG. 20 is a bottom view of the case 1600 in the open position. The case 1600 may be formed of a plastic, resin, or other polymeric shell, such that the case forms a housing for the whitening light 1100. As shown in FIG. 20, and in some embodiments, the case 1600 may include a bottom surface 2000. The bottom surface 2000 may be constructed of a rubber, silicone, or other non-slip material. In use, the case 1600 may be placed on a flat surface (such as a counter in a bathroom near a sink) such that the bottom surface 2000 interfaces with the flat surface. The user may open the case 1600 one handed (e.g., by pressing the cover 1602 with a finger or hand while pressing the case 1600 against the surface) since the bottom surface 2000 is constructed of a non-slip material, and thereby produces surface tension between the bottom surface 2000 and flat surface.

The case 1600 may include a movable cover 1602. The movable cover 1602 may move or transition between an open position (shown in FIG. 16) and closed position (shown in FIG. 17). When the movable cover 1602 is positioned in the open position, the case 1600 may be open to expose a cavity 1604 configured to house the whitening light 1100. When the movable cover 1602 is located in the closed position, the case 1600 may conceal, seal, or lock the cavity 1604. In some embodiments, the movable cover 1602 may transition between the open position and closed position via a slide, as shown in FIG. 19 and FIG. 20. For example, a user may push the movable cover 1602 open along axis A of FIG. 16, to expose the cavity 1604. The user may push or slide the movable cover 1602 along a track 2002 formed along an underside 2004 of the movable cover 1602. As shown in FIG. 19, as the movable cover 1602 is pushed open, the movable cover 1602 may slide upwardly and away from the cavity 1604. While this embodiment is shown, it is noted that the cover 1602 may transition between the open and closed position via other opening mechanisms, such as via a joint or hinge, a pivot, etc. In some embodiments, the cover 1602 may be biased in a fully open and fully closed position via a clasp or magnets. For example, the cover 1602 may include a magnet at opposite ends of the track 2002, and the case 1600 may include a magnet along an edge of the case 1600. In use, as the cover 1602 is slid closed (or slid open), the magnets at the ends of the track 2002 may engage with the magnet of the case 1600 to lock the cover 1602 to the case 1600 (e.g., in the open or closed position). While magnets are described, it is noted that the case 1600 may use bars or tabs, clips, or other locking mechanisms to bias the cover 1602 in the fully open or fully closed position.

As shown in FIG. 16, the whitening light 1100 may be configured to be positioned in (and removed from) a cavity 1604 formed within the case 1600. For example, a user may push the whitening light 1100 into the cavity 1604 such that the whitening light 1100 sits fully within the cavity 1604. The user may subsequently remove the whitening light 1100 using a detent 1606 arranged along a side of (and extending outwardly from) the cavity 1604.

When the whitening light 1100 is positioned within the cavity 1604, the case 1600 may be configured to charge the whitening light 1100. For example, the case 1600 may have a power source (such as a battery pack or bank of rechargeable batteries) which is configured to transfer power to the power source of the whitening light 1100. As one example, the case 1600 may have charging mechanism which align with the charging mechanism 1400 of the whitening light 1100 when the whitening light 1100 is positioned in the cavity 1604 of the case 1600. The case 1600 may be configured to transfer power between the charging mechanism of the case 1600 and the charging mechanism 1400 of the whitening light 1100 to thereby charge the power source of the whitening light 1100.

As can be best seen in FIG. 18, the case 1600 may include a port 1800. In some embodiments, the port 1800 may be arranged along a back side of the case 1600 as shown in FIG. 18. In some embodiments, the port 1800 may be arranged along a bottom of the case 1600. The port 1800 may be configured to receive an adapter for charging the power source of the case 1600, which in turn charges the whitening light 1100. The port 1800 may be similar in some regards to the port 1500 of the whitening light 1100. The port 1800 may be configured to receive a USB type-C adapter, micro-USB adapter, or other adapter configured to transfer power from an external power source (such as a battery pack, a wall outlet, a computer or mobile device, etc.) to the power source of the case 1600.

In some embodiments, the case 1600 may include an indicator light 1608 arranged near the backside of the cavity 1604 adjacent the rear portion 1104 of the whitening light 1100 (e.g., when the whitening light 1100 is situated in the cavity 1604). In some embodiments, the case 1600 may include the indicator light 1608 within the interior portion of the case 1600 as shown in FIG. 16, and an indicator light 1700 arranged along the cover 1602. The indicator light 1608, 1700 may be configured to indicate a charging status for the whitening light 1100 and/or the case 1600. The indicator light 1608, 1700 may indicate that charging of the whitening light 1100 is in progress, that charging of the whitening light 1100 is complete, and/or that the case 1600 has low power. For example, a controller of the case 1600 may be configured to control the indicator light 1608, 1700 to output light in a first color (e.g., red) when charging of the whitening light 1100 is commenced. Similarly, the controller may be configured to control the indicator light 1608, 1700 to output light in a second color (e.g., green) when charging of the whitening light 1100 is complete. Additionally, where the power source of the case 1600 requires recharging, the controller may be configured to control the indicator light 1608, 1700 to output light in another color or pattern (e.g., blinking red, blinking white, etc.).

Figure 21:
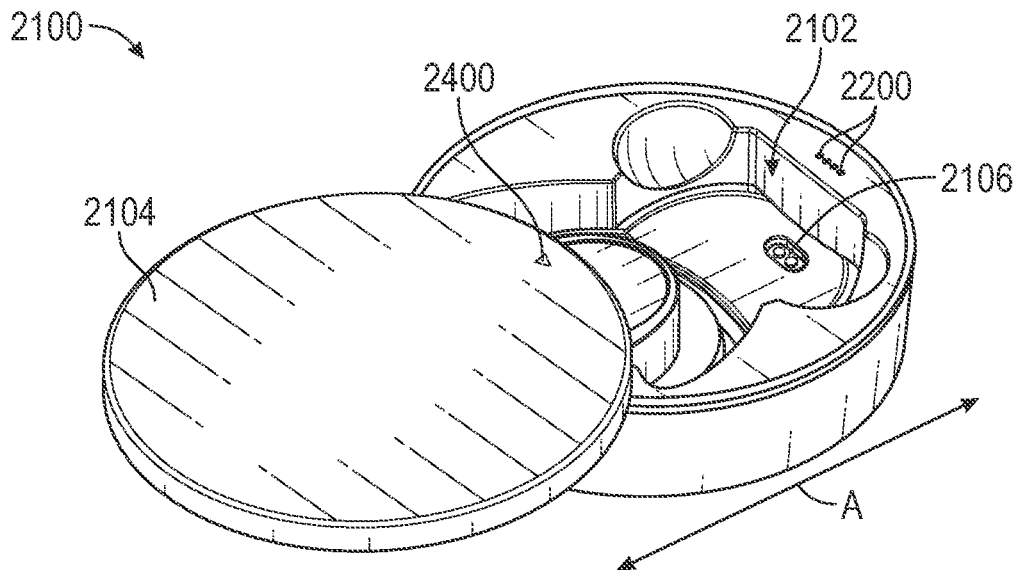
FIG. 21 is a perspective open view of a case for a whitening light, according to another exemplary embodiment.
Figure 22:
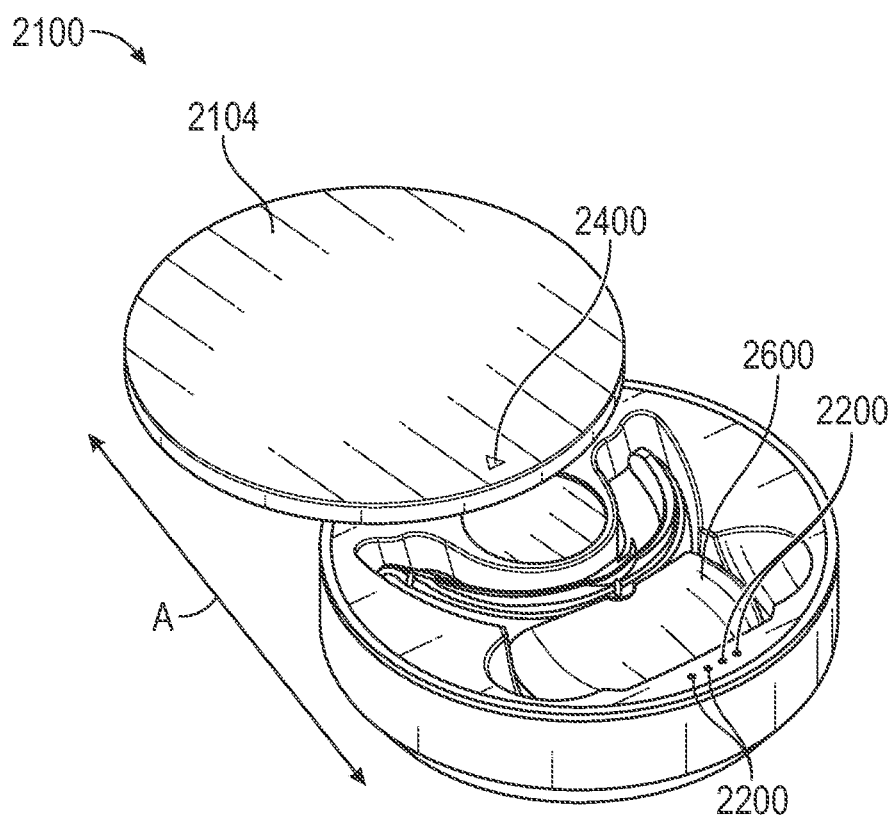
FIG. 22 is a perspective view of the case of FIG. 21 with a whitening light positioned therein, according to an exemplary embodiment.
Figure 23:
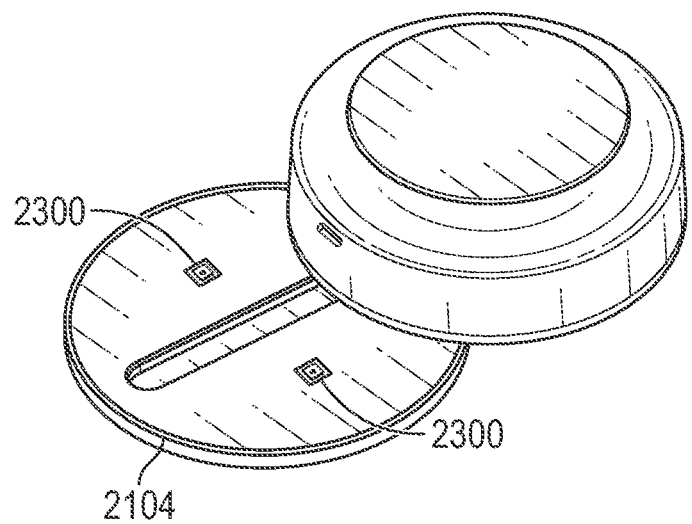
FIG. 23 is a perspective view of an underside of the case of FIG. 21, according to an exemplary embodiment.
Figure 24:
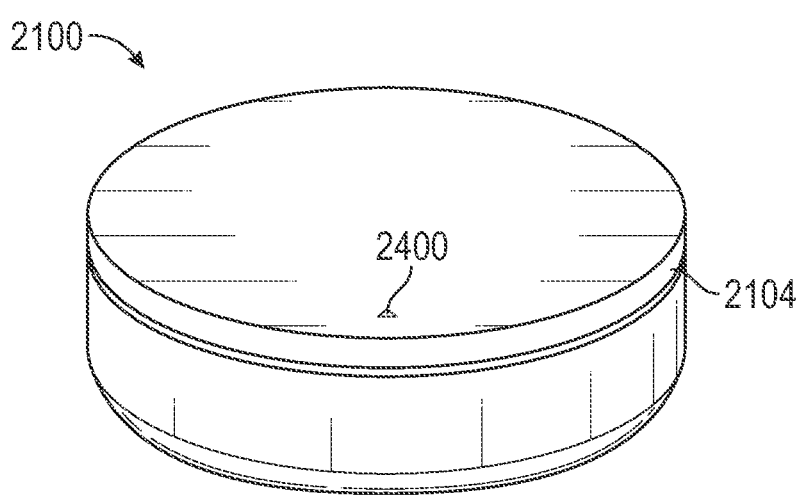
FIG. 24 is a perspective closed view of the case of FIG. 21, according to an exemplary embodiment.
Figure 25:
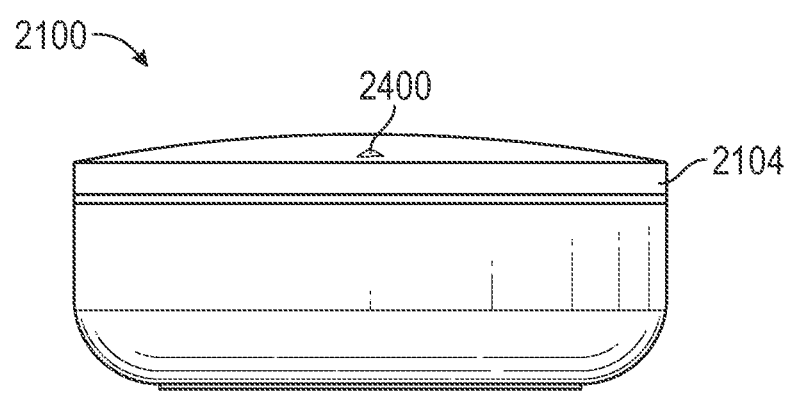
FIG. 25 is a side view of the case of FIG. 21, according to an exemplary embodiment.
Figure 26:
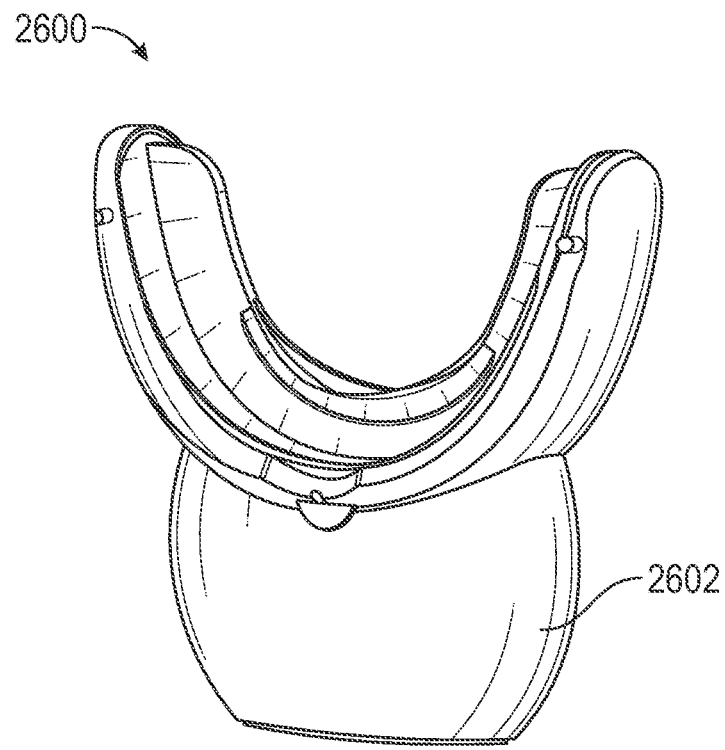
FIG. 26 is a perspective front view of the whitening light shown in FIG. 22, according to an exemplary embodiment.
Figure 27:
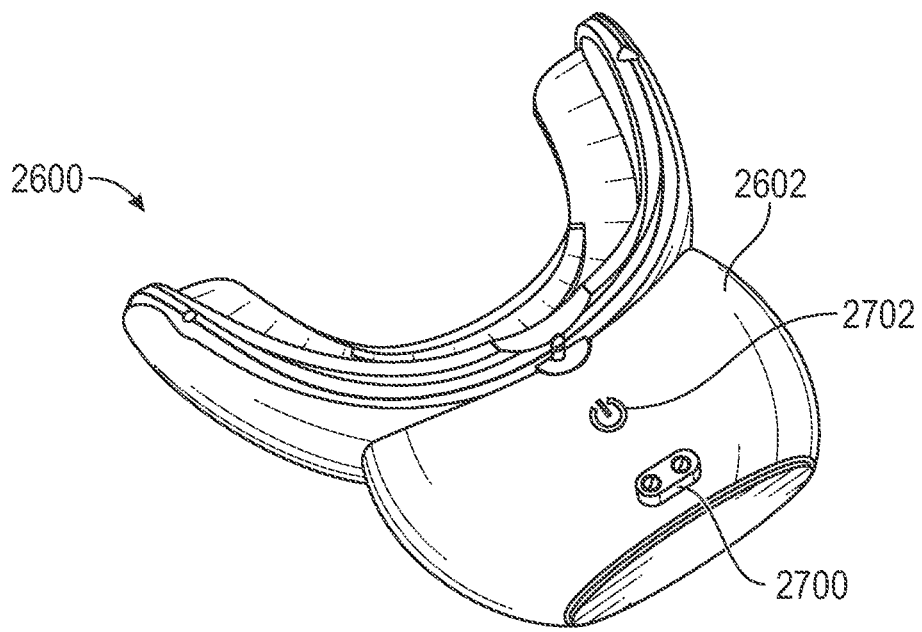
FIG. 27 is a perspective back view of the whitening light of FIG. 22, according to an exemplary embodiment.

Referring now to FIG. 21-FIG. 27, depicted are views of another embodiment of a case 2100 for a whitening light 2600, according to illustrative embodiments. Specifically, FIG. 21 shows a perspective open view of a case 2100, FIG. 22 shows a perspective view of the case 2100 with a whitening light 2600 positioned therein, FIG. 23 is a perspective view of an underside of the case 2100, FIG. 24 is a perspective closed view of the case 2100, FIG. 25 is a side view of the case 2100, FIG. 26 is a perspective front view of the whitening light 2600, and FIG. 27 is a perspective back view of the whitening light 2600, according to illustrative embodiments.

The case 2100 and whitening light 2600 may be similar in some respects to the case 1600 and whitening light 1100 described above with reference to FIG. 11-FIG. 20. For example, the case 2100 may include a cavity 2102 which is sized to receive the whitening light 2600. The case 2100 may also include a movable cover 2104 which moves between an open position shown in FIG. 21 and FIG. 22 to a closed position shown in FIG. 24. The movable cover 2104 may move (or slide) along the axis A shown in FIG. 22 between the open and closed positions, to selectively expose the cavity 2102. When the whitening light 2600 is situated in the cavity 2102 of the case 2100, power may be transferred from a power source of the case 2100 to a power source of the whitening light 2600, to charge the whitening light 2600.

The case 2100 may include indicator lights 2200 situated adjacent the cavity 2102, as well as an indicator light 2400 situated on the movable cover 2104. The indicator lights 2200, 2400 may indicate a charging status of the whitening light 2600 and/or the case 2100.

In the embodiment shown in FIG. 21-FIG. 27, the whitening light 2600 may include charging mechanism 2700 (e.g., one or more charging plate, charging pin, requiring contact or by no contact charging, etc.) situated on a backside of the rear portion 2602 of the whitening light 2600. Similarly, the case 2100 may include charging mechanism 2106 arranged on an upwardly-facing surface of the cavity 2102. The charging mechanism 2106 may be situated at a location which corresponds to a location of the charging mechanism 2700 located on the whitening light 2600. When the whitening light 2600 is located in the cavity 2102, the charging mechanism 2700 of the whitening light 2600 may be aligned with the charging mechanism 2106 of the case 2100 such that the charging mechanism 2700, 2106 are in contact with one another, to transfer power from the case 2100 to the whitening light 2600 (e.g., via the charging mechanism 2700, 2106).

In some embodiments, the case 2100 may include one or more sterilization lights 2300. The sterilization lights 2300 may be situated on an underside of the movable cover 2104. In some embodiments, the sterilization lights 2300 may be configured to sterilize the whitening light 2600 when the whitening light 2600 is situated in the cavity 2102. The sterilization lights 2300 may be situated at a location which corresponds to (e.g., is overhead) the cavity 2102 when the movable cover 2104 is located in the closed position (shown in FIG. 24). The sterilization lights 2300 may be automatically activated (e.g., by a processor of the case 2100) when the movable cover 2104 is in the closed position and the whitening light 2600 is located in the cavity 2102 (e.g., as evidenced by charging the whitening light 2600). The sterilization lights 2300 may be or include an ultraviolet (UV) light source configured to output UV light towards the whitening light 2600. Such embodiments may clean the whitening light 2600 while the whitening light 2600 is charging.

In some embodiments, the whitening light 2600 may include a power button 2702. The power button 2702 may be situated near the charging mechanism 2700 of the whitening light 2600 (e.g., on a backside of the rear portion 2602 of the whitening light 2600). The power button 2702 may control output of lights from LEDs of the whitening light 2600. For example, rather than automatically activating when the whitening light 2600 is removed from the cavity 2102, the user may position the whitening light 2600 in their mouth, and select the power button 2702 to turn on the whitening light 2600 for the predetermined duration. Following the predetermined duration elapsing, the whitening light 2600 may automatically be deactivated, the charge of the whitening light may be depleted to deactivate the whitening light 2600, a feedback device of the whitening light 2600 may alert the user to turn off the whitening light 2600, etc.

Figure 28:
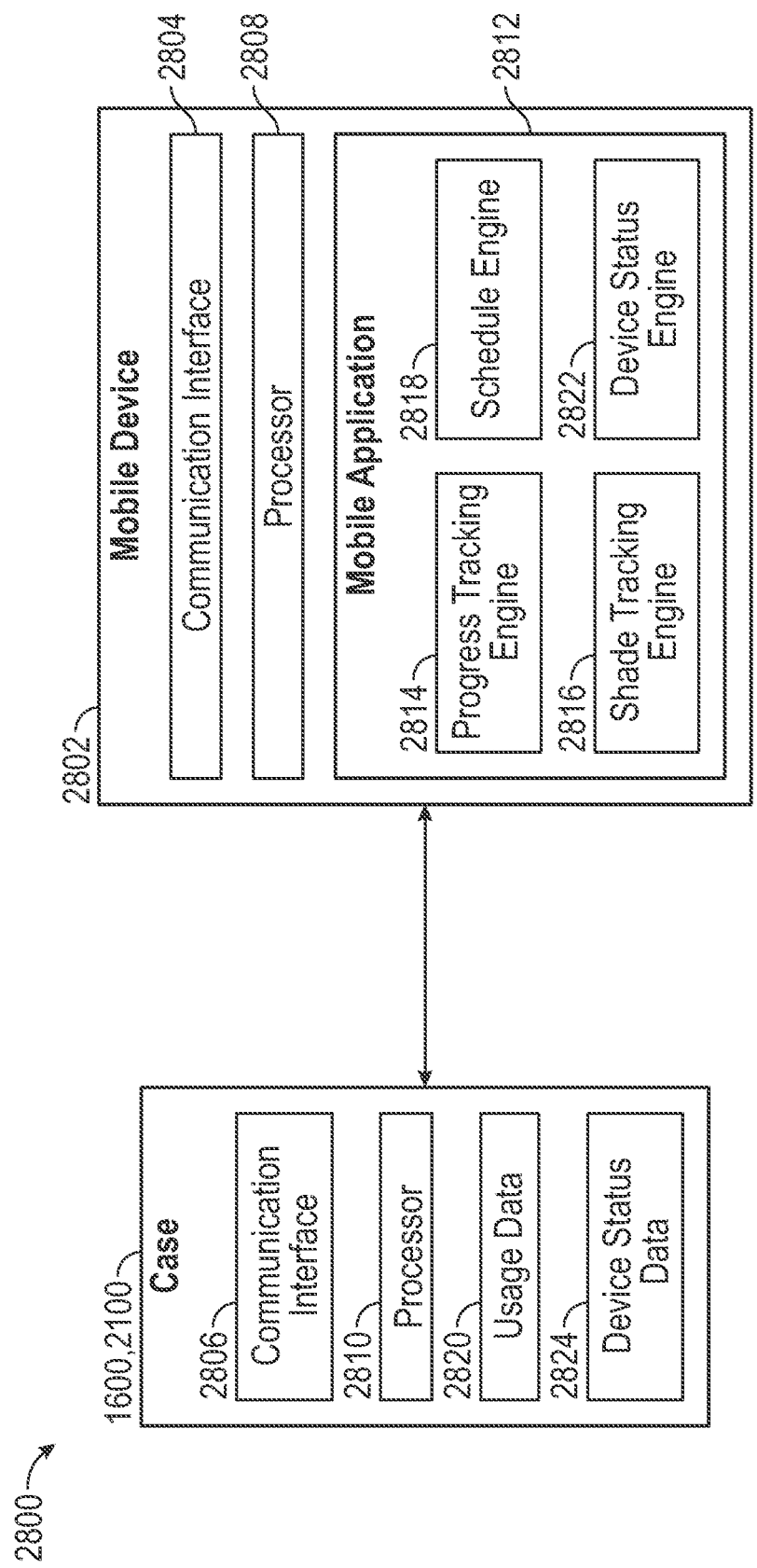
FIG. 28 is a block diagram of a computing environment, according to an exemplary embodiment.

Referring now to FIG. 28, depicted is a computing environment in which a user can control the whitening light and track use thereof, according to an illustrative embodiment. As shown in FIG. 28, the computing environment 2800 may include a mobile device 2802 and the case 1600. The mobile device 2802 and case 1600 may each include a communication interface 2804, 2806, and processor 2808, 2810. The communication interface 2804, 2806 may be any device(s) or component(s) designed or configured to facilitate wireless exchange of data. For example, the communication interfaces 2804, 2806 may be or include components which facilitate communication via BLUETOOTH, WIFI, near-field communication (NFC), etc.

The processors 2808, 2810 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. The processors 2808, 2810 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function.

The processor 2808 of the mobile device 2802 may be configured to implement a mobile application 2812 which corresponds to the whitening light 1100 and/or case 1600. In some embodiments, the processor 2808 may be configured to access the mobile application 2812 via the internet (e.g., the mobile application 2812 may be a cloud-based or internet-based application). In either embodiment, a user may use the mobile application 2812, for example, track the user's use of the whitening light 1100, upload photos, track the shading of the user's teeth, view a schedule for whitening, and determine/configure a device status. For example, the mobile application 2812 may include a progress tracking engine 2814, a shade tracking engine 2816, a schedule engine 2818, and a device status engine 2822. Each of the engines may be or include a combination of hardware and software configured to receive inputs/provide data corresponding to the whitening light 1100, the case 1600, and/or a user's progress in using the whitening light 1100. The mobile application 2812 may be configured to receive data from and transmit data to the case 1600 for controlling or monitoring the case 1600, the whitening light 1100, and so forth.

In some embodiments, the application 2812 includes a progress tracking engine 2814. The progress tracking engine 2814 may be any device, component, script, or combination of hardware and software designed or implemented to track a user's whitening progress. In some embodiments, the progress tracking engine 2814 may be configured to receive one or more progress photos captured by the user of the user's teeth. The progress photos may be taken at various stages of the whitening process (e.g., a first photo prior to treatment, one or more intermediate photos during treatment, and a completion photo once the user has completed a whitening treatment session or group of whitening treatment sessions). The progress tracking engine 2814 may be configured to receive the photos uploaded by the user. The progress tracking engine 2814 may be configured to generate a user interface which displays the series of photos from the first photo through the completion photo on the mobile device 2802. In some embodiments, the progress tracking engine 2814 may be communicably coupled (e.g., via an application program interface (API)) to one or more social media accounts of the user such that the user may upload the series of photos to social media.

In some embodiments, the application 2812 includes a shade tracking engine 2816. The shade tracking engine 2816 may be any device, component, script, or combination of hardware and software designed or implemented to track, map, determine, or predict a shade of the user's teeth. In some embodiments, the shade tracking engine 2816 may be configured to determine a first shade using the first photo uploaded by the user (e.g., to the progress tracking engine 2814). The shade tracking engine 2816 may be configured to analyze, inspect, or otherwise parse the first photo uploaded by the user to identify the user's teeth in the image (e.g., by identifying a change contrast between the user's lips or gums and teeth, using object detection or model matching, etc.). The shade tracking engine 2816 may be configured to determine the shade by matching one or more known shades (e.g., stored, maintained, included, or otherwise accessible by the shade tracking engine 2816) with a shade of the user's teeth. The shade tracking engine 2816 may assign the first image the matched shade. The shade tracking engine 2816 may similarly assign the intermediate images and completion images a shade based on matching a known shade with the shade of the user's teeth in such images.

In some embodiments, the shade tracking engine 2816 may be configured to predict a final (or completion shade) based on the progress of the user. For example, the shade tracking engine 2816 may be configured to predict the final shade based on a delta between the shade of the user's teeth in the first image and the shade of the user's teeth in the intermediate image(s). The shade tracking engine 2816 may be configured to compare the delta with one or more models (generated based on historical data corresponding to whitening treatment) to determine a likely final shade for the user. In some embodiments, the shade tracking engine 2816 may be configured to generate a notification or prompt for the user which indicates the likely or predicted final shade for the user.

In some embodiments, the application 2812 may include a schedule engine 2818. The schedule engine 2818 may be any device, component, script, or combination of hardware and software designed or implemented to maintain and track a whitening schedule for the user. The schedule engine 2818 may be configured to generate the schedule based on a known start date for the user. The schedule may be, for example, once a day, once every other day, etc., for a predetermined duration, which may be a week, two weeks, a month, etc. The schedule engine 2818 may be configured to track a user's adherence to the schedule. For example, the schedule engine 2818 may be configured to receive usage data 2820 from the case 1600. The processor 2810 of the case 1600 may be configured to generate usage data 2820 once the whitening light 1100 is removed from the case 1600 (indicating the whitening light 1100 is being used). The processor 2810 may be configured to transmit the usage data 2820 via the communication interface 2806 to the communication interface 2804 of the mobile device 2802.

The schedule engine 2818 may be configured to track or determine whether the user is adhering to the whitening schedule based on the usage data 2820 from the case 1600. For example, the schedule engine 2818 may be configured to compare a timestamp for the usage data 2820 to the whitening schedule to determine whether the user is whitening their teeth once a day, once every other day, etc. in accordance with the whitening schedule. In some embodiments, where the user is not adhering to the whitening schedule, the scheduling engine 2818 may be configured to generate a prompt, reminder, alarm, or other alert which reminds or triggers the user to whiten their teeth. For example, where the user has not used the whitening light 1100 in 24 hours, the scheduling engine 2818 may be configured to generate an alert which reminds the user to whiten their teeth. As another example, the scheduling engine 2818 may be configured to generate a daily alarm or alert which reminds the user to use the whitening light 1100 at the same time each day. Such embodiments may provide for better adherence to the whitening schedule.

In some embodiments, the application 2812 may include a device status engine 2822. The device status engine 2822 may be any device, component, script, or combination of hardware and software designed or implemented to track, determine, or modify a status of the case 1600 and/or whitening light 1100. For example, the device status engine 2822 may be configured to receive and display device status data 2824 received from the case 1600 (in a manner similar to receiving the usage data 2820). The device status data 2824 may include, for example, a charging status of the case 1600 (e.g., currently charging, percentage battery remaining duration until fully charged, etc.), a charging status of the whitening light 1100, whether the whitening light 1100 is on or off, a color of the light output by the whitening light 1100, and so forth. The device status engine 2822 may be configured to generate a user interface which displays a status of the case 1600 and/or the whitening light 1100. In some embodiments, one or more statuses may be modified by a user. For example, a user may select a button or drop-down menu item to modify a status of the whitening light 1100 (e.g., to turn on or off the whitening light 1100, to change a color of the light output by the LEDs 1106, to change the duration of a whitening treatment session, etc.).

The device status engine 2822 may receive the user selection on the user interface. The device status engine 2822 may be configured to modify, change, update, or otherwise cause the status of the device (e.g., whitening light 1100 or case 1600) to change according to the user selection. For example, the device status engine 2822 may be configured to transmit instructions via the communications interfaces 2804, 2806 to the case 1600 for the processor 2810 of the case 1600. The processor 2810 may receive the instructions for execution. The processor 2810 may execute the instructions to update the status of the case 1600 or whitening light 1100. For example, the processor 2810 may execute the instructions to cause the whitening light 1100 to turn on or turn off according to the user selection. As another example, the processor 2810 may execute instructions to cause the whitening light 1100 to output light in a different color scheme (e.g., from blue, to a mixture of blue and purple, to green, to red, etc.). Accordingly, the user may be able to modify one or more settings for the whitening light 1100 using the application 2812.

The embodiments described herein have been described with reference to drawings. The drawings illustrate certain details of specific embodiments described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The construction and arrangement of the elements of the mouthpiece 100, whitening lights 1100, 2600, and cases 1600, 2100 as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, use of materials, colors, orientations, etc.) without materially departing from the novel teachings and advantages of the subject matter recited. For example, elements shown as integrally formed may be constructed of multiple parts or elements, the position of elements may be reversed or otherwise varied, and the nature or number of discrete elements or positions may be altered or varied.

The word "exemplary" is used to mean serving as an example, instance, or illustration. Any embodiment or design described herein as "exemplary" or as an "example" is not necessarily to be construed as preferred or advantageous over other embodiments or designs (and such term is not intended to connote that such embodiments are necessarily extraordinary or superlative examples). Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

Other substitutions, modifications, changes and omissions may also be made in the design, operating conditions and arrangement of the various exemplary embodiments without departing from the scope of the present invention. For example, any element disclosed in one embodiment may be incorporated or utilized with any other embodiment disclosed herein. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration, and arrangement of the preferred and other exemplary embodiments without departing from the scope of the appended claims.

What is claimed is:

1. A whitening light comprising:
   a mouthpiece having a first light array arranged along a lower portion of the mouthpiece for directing light onto an exposed portion of a plurality of lower teeth of a user and a second light array arranged along an upper portion of the mouthpiece for directing light onto an exposed portion of a plurality of upper teeth of the user; and
   a rear portion comprising a first power source and a first charging mechanism, the first power source communicably coupled to the first light array and the second light array, the first charging mechanism configured to receive power transferred from a second charging mechanism located on a case for the whitening light, wherein the first power source comprises a rechargeable battery configured to be charged by the second charging mechanism, the rechargeable battery being charged to a power output sufficient to power the whitening light to automatically activate the first light array and the second light array to emit light configured to whiten teeth upon selection of a button on the rear portion of the whitening light to commence a treatment session, to emit the light for a predetermined duration corresponding to a duration of the treatment session, and to automatically switch the first light array and the second light array to an off-setting following expiration of the predetermined duration.

2. The whitening light of claim 1, wherein the case further comprises a second power source and a cavity sized to receive the mouthpiece, and wherein the second charging mechanism is communicably coupled to the second power source and configured to electrically couple with the first charging mechanism to transfer power from the second power source to the first power source when the whitening light is positioned in the cavity.

3. The whitening light of claim 1, wherein the first light array includes at least ten lights arranged to direct light onto at least ten lower teeth.

4. The whitening light of claim 1, wherein the second light array includes at least ten lights arranged to direct light onto at least ten upper teeth.

5. The whitening light of claim 1, wherein the mouthpiece and the rear portion together define a profile of the whitening light that matches a shape of a cavity of the case.

6. The whitening light of claim 5, wherein the first charging mechanism is positioned on a first side of the rear portion of the whitening light, and wherein the second charging mechanism is positioned in the cavity at a location that corresponds to the first charging mechanism when the whitening light is positioned in the cavity of the case.

7. The whitening light of claim 6, wherein the button is located on a second side of the rear portion opposite the first side.

8. The whitening light of claim 6, wherein the first charging mechanism is aligned with the second charging mechanism when the whitening light is positioned in the cavity of the case.

9. The whitening light of claim 8, wherein the first charging mechanism and the second charging mechanism comprise respective charging plates that form an electrical contact when the whitening light is positioned in the cavity of the case, and wherein the power from the case is transferred via the second charging mechanism through the electrical contact to the first charging mechanism to charge the whitening light.

10. The whitening light of claim 1, wherein the first light array is separated from the second light array by a distance in the range of 8 to 10 millimeters.

11. A whitening light comprising:
a mouthpiece having a light array arranged along the mouthpiece for directing light onto an exposed portion of a plurality of teeth of a user; and
a rear portion comprising a first power source and a first charging mechanism, the first power source communicably coupled to the light array, the first charging mechanism configured to receive power transferred from a second charging mechanism located on a case for the whitening light, wherein the first power source comprises a rechargeable battery configured to be charged by the second charging mechanism, the rechargeable battery configured to be charged to a power output sufficient to power the whitening light to emit light configured to whiten teeth upon selection of a button on the rear portion of the whitening light to commence a treatment session, to emit the light for a predetermined duration corresponding to a duration of the treatment session, and to automatically switch the light array to an off-setting following expiration of the predetermined duration.

12. The whitening light of claim 11, wherein the case further comprises a second power source and a cavity sized to receive the mouthpiece, and wherein the second charging mechanism is communicably coupled to the second power source and configured to electrically couple with the first charging mechanism to transfer power from the second power source to the first power source when the whitening light is positioned in the cavity.

13. The whitening light of claim 11, wherein the light array includes at least ten lights arranged to direct light onto at least ten lower teeth and at least ten lights arranged to direct light onto at least ten upper teeth.

14. The whitening light of claim 11, wherein the mouthpiece and the rear portion together define a profile of the whitening light that matches a shape of a cavity of the case.

15. The whitening light of claim 14, wherein the first charging mechanism is positioned on a first side of the rear portion of the whitening light, and wherein the second charging mechanism is positioned in the cavity at a location that corresponds to the first charging mechanism when the whitening light is positioned in the cavity of the case.

16. The whitening light of claim 15, wherein the first charging mechanism is aligned with the second charging mechanism when the whitening light is positioned in the cavity of the case.

17. The whitening light of claim 16, wherein the first charging mechanism and the second charging mechanism comprise respective charging plates that form an electrical contact when the whitening light is positioned in the cavity of the case, and wherein the power from the case is transferred via the second charging mechanism through the electrical contact to the first charging mechanism to charge the whitening light.

18. The whitening light of claim 14, wherein the button is located on a second side of the rear portion opposite the first side.

19. The whitening light of claim 11, wherein the light array is a first light array and the first light array is separated from a second light array by a distance in the range of 8 to 10 millimeters.

20. A whitening light comprising:
a mouthpiece having a light array arranged along the mouthpiece for directing light onto an exposed portion of a plurality of teeth of a user; and
a rear portion comprising a first power source and a first charging mechanism including a first charging plate, the first power source communicably coupled to the light array, the first charging mechanism configured to receive power transferred via the first charging plate from a second charging plate of a second charging mechanism located on a case for the whitening light, wherein the power is transferred from the second charging plate to the first charging plate responsive to the first charging plate and the second charging plate forming an electrical contact when the whitening light is positioned in the case, wherein the first power source comprises a rechargeable battery configured to be charged by the second charging mechanism, the rechargeable battery being charged to a power output sufficient to power the whitening light to emit light configured to whiten teeth upon selection of a button on the rear portion of the whitening light to commence a treatment session, to emit the light for a predetermined duration corresponding to a duration of the treatment session, and to automatically switch the light array to an off-setting following expiration of the predetermined duration.

* * * * *